(12) United States Patent
Amin et al.

(10) Patent No.: US 9,770,232 B2
(45) Date of Patent: Sep. 26, 2017

(54) HEART OCCLUSION DEVICES

(75) Inventors: Zahid Amin, Omaha, NE (US);
Edward H. Cully, Flagstaff, AZ (US);
Warren Cutright, Flagstaff, AZ (US);
Coby Larsen, Flagstaff, AZ (US);
Steven J. Masters, Flagstaff, AZ (US);
Edward Emil Shaw, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 320 days.

(21) Appl. No.: 13/571,046

(22) Filed: Aug. 9, 2012

(65) Prior Publication Data
US 2013/0041404 A1    Feb. 14, 2013

Related U.S. Application Data

(60) Provisional application No. 61/523,175, filed on Aug. 12, 2011.

(51) Int. Cl.
*A61F 2/02* (2006.01)
*A61B 17/00* (2006.01)
*A61B 17/12* (2006.01)

(52) U.S. Cl.
CPC .... *A61B 17/0057* (2013.01); *A61B 17/12031* (2013.01); *A61B 17/12145* (2013.01);
(Continued)

(58) Field of Classification Search
CPC ...... A61B 17/0057; A61B 2017/00243; A61B 2017/00592; A61B 2017/00606;
(Continued)

(56) References Cited

U.S. PATENT DOCUMENTS 283,653 A    8/1883   Paxson
3,294,631 A   12/1966  Lorenz et al.
(Continued)

FOREIGN PATENT DOCUMENTS

CN    1218379 A    6/1999
CN    101460102 A  6/2009
(Continued)

OTHER PUBLICATIONS

International Search Report and Written Opinion; Feb. 22, 2013; World Intellectual Property Organization (WIPO) (International Bureau of); PCT/US2012/050358; 15 pages.
(Continued)

*Primary Examiner* — Melanie Tyson

(57) ABSTRACT

Devices for occluding an aperture in tissue or a vessel include a first flexible wire and a second flexible wire. Each of the first and second wires is formed of a shape memory material. Each of the first and second wires is shaped into first and second geometric forms such that the first geometric form of the first wire and the first geometric form of the second wire form a first plate in a first plane, and the second geometric form of the first wire and the second geometric form of the second wire form a second plate in a second plane that is parallel to and remote from the first plane. The first and second plates are separated by a waist formed from two portions of the first wire and two portions of the second wire. Methods for occluding an aperture in tissue or a vessel using such devices are also provided.

19 Claims, 14 Drawing Sheets

(52) U.S. Cl.
CPC .............. *A61B 2017/00597* (2013.01); *A61B 2017/00606* (2013.01); *A61B 2017/00867* (2013.01)

(58) Field of Classification Search
CPC  A61B 2017/00623; A61B 2018/00273; A61B 2017/00575; A61B 2017/00588; A61B 2017/00597; A61B 2017/00615; A61B 2017/00619; A61B 2017/00628; A61B 2017/00632
USPC ....... 606/213, 215–219, 200, 151, 153, 157, 606/139, 232; 227/175.1, 1, 179.1, 181.1, 227/26, 28, 29, 30, 31, 19
See application file for complete search history.

(56) References Cited

U.S. PATENT DOCUMENTS

| | | |
|---|---|---|
| 3,324,518 A | 6/1967 | Louderback |
| 3,447,533 A | 6/1969 | Spicer |
| 3,739,770 A | 6/1973 | Mori |
| 3,824,631 A | 7/1974 | Burstein et al. |
| 3,874,388 A | 4/1975 | King et al. |
| 3,875,648 A | 4/1975 | Bone |
| 3,907,675 A | 9/1975 | Chapurlat et al. |
| 3,924,631 A | 12/1975 | Mancusi, Jr. |
| 3,939,849 A | 2/1976 | Baxter et al. |
| 4,006,747 A | 2/1977 | Kronenthal et al. |
| 4,007,743 A | 2/1977 | Blake |
| 4,038,365 A | 7/1977 | Patil et al. |
| 4,113,912 A | 9/1978 | Okita |
| 4,149,327 A | 4/1979 | Hammer et al. |
| 4,193,138 A | 3/1980 | Okita |
| 4,425,908 A | 1/1984 | Simon |
| 4,525,374 A | 6/1985 | Vaillancourt |
| 4,610,674 A | 9/1986 | Suzuki et al. |
| 4,619,246 A | 10/1986 | Molgaard et al. |
| 4,626,245 A | 12/1986 | Weinstein |
| 4,693,249 A | 9/1987 | Schenck et al. |
| 4,696,300 A | 9/1987 | Anderson |
| 4,710,181 A | 12/1987 | Fuqua |
| 4,710,192 A | 12/1987 | Liotta et al. |
| 4,738,666 A | 4/1988 | Fuqua |
| 4,766,898 A | 8/1988 | Hardy et al. |
| 4,796,612 A | 1/1989 | Reese |
| 4,832,055 A | 5/1989 | Palestrant |
| 4,836,204 A | 6/1989 | Landymore et al. |
| 4,840,623 A | 6/1989 | Quackenbush |
| 4,902,508 A | 2/1990 | Badylak et al. |
| 4,915,107 A | 4/1990 | Rebuffat et al. |
| 4,917,089 A | 4/1990 | Sideris |
| 4,917,793 A | 4/1990 | Pitt et al. |
| 4,921,479 A | 5/1990 | Grayzel |
| 4,956,178 A | 9/1990 | Badylak et al. |
| 5,021,059 A | 6/1991 | Kensey et al. |
| 5,037,433 A | 8/1991 | Wilk et al. |
| 5,041,129 A | 8/1991 | Hayhurst et al. |
| 5,041,225 A | 8/1991 | Norman |
| 5,049,131 A | 9/1991 | Deuss |
| 5,049,275 A | 9/1991 | Gillberg-LaForce et al. |
| 5,078,736 A | 1/1992 | Behl |
| 5,090,422 A | 2/1992 | Dahl et al. |
| 5,098,440 A | 3/1992 | Hillstead |
| 5,106,913 A | 4/1992 | Yamaguchi et al. |
| 5,108,420 A | 4/1992 | Marks |
| 5,149,327 A | 9/1992 | Oshiyama |
| 5,152,144 A | 10/1992 | Andrie |
| 5,163,131 A | 11/1992 | Row et al. |
| 5,167,363 A | 12/1992 | Adkinson et al. |
| 5,167,637 A | 12/1992 | Okada et al. |
| 5,171,259 A | 12/1992 | Inoue |
| 5,176,659 A | 1/1993 | Mancini |
| 5,192,301 A | 3/1993 | Kamiya et al. |
| 5,222,974 A | 6/1993 | Kensey et al. |
| 5,226,879 A | 7/1993 | Ensminger et al. |
| 5,234,458 A | 8/1993 | Metais |
| 5,236,440 A | 8/1993 | Hlavacek |
| 5,245,023 A | 9/1993 | Peoples et al. |
| 5,245,080 A | 9/1993 | Aubard et al. |
| 5,250,430 A | 10/1993 | Peoples et al. |
| 5,257,637 A | 11/1993 | El Gazayerli |
| 5,269,809 A | 12/1993 | Hayhurst et al. |
| 5,275,826 A | 1/1994 | Badylak et al. |
| 5,282,827 A | 2/1994 | Kensey et al. |
| 5,284,488 A | 2/1994 | Sideris |
| 5,304,184 A | 4/1994 | Hathaway et al. |
| 5,312,341 A | 5/1994 | Turi |
| 5,312,435 A | 5/1994 | Nash et al. |
| 5,316,262 A | 5/1994 | Koebler |
| 5,320,611 A | 6/1994 | Bonutti et al. |
| 5,334,217 A | 8/1994 | Das |
| 5,342,393 A | 8/1994 | Stack |
| 5,350,363 A | 9/1994 | Goode et al. |
| 5,350,399 A | 9/1994 | Erlebacher et al. |
| 5,354,308 A | 10/1994 | Simon et al. |
| 5,364,356 A | 11/1994 | Hofling |
| 5,397,331 A | 3/1995 | Himpens et al. |
| 5,411,481 A | 5/1995 | Allen et al. |
| 5,413,584 A | 5/1995 | Schulze |
| 5,417,699 A | 5/1995 | Klein et al. |
| 5,425,744 A | 6/1995 | Fagan et al. |
| 5,433,727 A | 7/1995 | Sideris |
| 5,437,288 A | 8/1995 | Schwartz et al. |
| 5,443,727 A | 8/1995 | Gagnon |
| 5,451,235 A | 9/1995 | Lock et al. |
| 5,453,099 A | 9/1995 | Lee et al. |
| 5,478,353 A | 12/1995 | Yoon |
| 5,480,353 A | 1/1996 | Garza, Jr. |
| 5,480,424 A | 1/1996 | Cox |
| 5,486,193 A | 1/1996 | Bourne et al. |
| 5,507,811 A | 4/1996 | Koike et al. |
| 5,534,432 A | 7/1996 | Peoples et al. |
| 5,540,712 A | 7/1996 | Kleshinski et al. |
| 5,549,959 A | 8/1996 | Compton |
| 5,562,632 A | 10/1996 | Davila et al. |
| 5,562,728 A | 10/1996 | Lazarus et al. |
| 5,571,169 A | 11/1996 | Plaia et al. |
| 5,575,816 A | 11/1996 | Rudnick et al. |
| 5,577,299 A | 11/1996 | Thompson et al. |
| 5,578,045 A | 11/1996 | Das |
| 5,591,206 A | 1/1997 | Moufarrege |
| 5,601,571 A | 2/1997 | Moss |
| 5,603,703 A | 2/1997 | Elsberry et al. |
| 5,618,311 A | 4/1997 | Gryskiewicz |
| 5,620,461 A | 4/1997 | Muijs Van De Moer et al. |
| 5,626,599 A | 5/1997 | Bourne et al. |
| 5,634,936 A | 6/1997 | Linden et al. |
| 5,649,950 A | 7/1997 | Bourne et al. |
| 5,649,959 A | 7/1997 | Hannam et al. |
| 5,662,701 A | 9/1997 | Plaia et al. |
| 5,663,063 A | 9/1997 | Peoples et al. |
| 5,683,411 A | 11/1997 | Kavteladze et al. |
| 5,690,674 A | 11/1997 | Diaz |
| 5,693,085 A | 12/1997 | Buirge et al. |
| 5,702,421 A | 12/1997 | Schneidt |
| 5,709,707 A | 1/1998 | Lock et al. |
| 5,713,864 A | 2/1998 | Verkaart |
| 5,713,948 A | 2/1998 | Uflacker |
| 5,717,259 A | 2/1998 | Schexnayder |
| 5,720,754 A | 2/1998 | Middleman et al. |
| 5,725,552 A | 3/1998 | Kotula et al. |
| 5,725,553 A | 3/1998 | Moenning |
| 5,733,294 A | 3/1998 | Forber et al. |
| 5,733,337 A | 3/1998 | Carr, Jr. et al. |
| 5,741,297 A | 4/1998 | Simon |
| 5,749,880 A | 5/1998 | Banas et al. |
| 5,755,762 A | 5/1998 | Bush |
| 5,769,882 A | 6/1998 | Fogarty et al. |
| 5,772,641 A | 6/1998 | Wilson |
| 5,776,162 A | 7/1998 | Kleshinski |
| 5,776,183 A | 7/1998 | Kanesaka et al. |
| 5,782,847 A | 7/1998 | Plaia et al. |
| 5,782,860 A | 7/1998 | Epstein et al. |
| 5,797,960 A | 8/1998 | Stevens et al. |

(56) References Cited

U.S. PATENT DOCUMENTS

| | | |
|---|---|---|
| 5,799,384 A | 9/1998 | Schwartz et al. |
| 5,800,436 A | 9/1998 | Lerch |
| 5,800,516 A | 9/1998 | Fine et al. |
| 5,810,884 A | 9/1998 | Kim |
| 5,820,594 A | 10/1998 | Fontirroche et al. |
| 5,823,956 A | 10/1998 | Roth et al. |
| 5,829,447 A | 11/1998 | Stevens et al. |
| 5,835,422 A | 11/1998 | Merritt |
| 5,853,420 A | 12/1998 | Chevillon et al. |
| 5,853,422 A | 12/1998 | Huebsch et al. |
| 5,855,614 A | 1/1999 | Stevens et al. |
| 5,861,003 A | 1/1999 | Latson et al. |
| 5,865,791 A | 2/1999 | Whayne et al. |
| 5,865,844 A | 2/1999 | Plaia et al. |
| 5,873,905 A | 2/1999 | Plaia et al. |
| 5,879,366 A | 3/1999 | Shaw et al. |
| 5,893,856 A | 4/1999 | Jacob et al. |
| 5,895,411 A | 4/1999 | Irie |
| 5,897,955 A | 4/1999 | Drumheller |
| 5,902,287 A | 5/1999 | Martin |
| 5,902,319 A | 5/1999 | Daley |
| 5,902,745 A | 5/1999 | Butler et al. |
| 5,904,703 A | 5/1999 | Gilson |
| 5,906,639 A | 5/1999 | Rudnick et al. |
| 5,919,200 A | 7/1999 | Stambaugh et al. |
| 5,924,424 A | 7/1999 | Stevens et al. |
| 5,925,060 A | 7/1999 | Forber |
| 5,928,250 A | 7/1999 | Koike et al. |
| 5,944,691 A | 8/1999 | Quems et al. |
| 5,944,738 A | 8/1999 | Amplatz et al. |
| 5,955,110 A | 9/1999 | Patel et al. |
| 5,957,490 A | 9/1999 | Sinnhuber |
| 5,957,953 A | 9/1999 | DiPoto et al. |
| 5,967,490 A | 10/1999 | Pike |
| 5,976,174 A | 11/1999 | Ruiz |
| 5,980,505 A | 11/1999 | Wilson |
| 5,989,268 A | 11/1999 | Pugsley, Jr. et al. |
| 5,993,475 A | 11/1999 | Lin et al. |
| 5,993,844 A | 11/1999 | Abraham et al. |
| 5,997,575 A | 12/1999 | Whitson et al. |
| 6,010,517 A | 1/2000 | Baccaro |
| 6,016,846 A | 1/2000 | Knittel et al. |
| 6,019,753 A | 2/2000 | Pagan |
| 6,024,756 A | 2/2000 | Huebsch et al. |
| 6,027,519 A | 2/2000 | Stanford |
| 6,030,007 A | 2/2000 | Bassily et al. |
| 6,051,007 A | 4/2000 | Hogendijk et al. |
| 6,053,939 A | 4/2000 | Okuda et al. |
| 6,056,760 A | 5/2000 | Koike et al. |
| 6,071,998 A | 6/2000 | Muller et al. |
| 6,074,401 A | 6/2000 | Gardiner et al. |
| 6,077,291 A | 6/2000 | Das |
| 6,077,880 A | 6/2000 | Castillo et al. |
| 6,079,414 A | 6/2000 | Roth |
| 6,080,182 A | 6/2000 | Shaw et al. |
| 6,080,183 A | 6/2000 | Tsugita et al. |
| 6,096,347 A | 8/2000 | Geddes et al. |
| 6,106,913 A | 8/2000 | Scardino et al. |
| 6,113,609 A | 9/2000 | Adams |
| 6,117,159 A | 9/2000 | Huebsch et al. |
| 6,123,715 A | 9/2000 | Amplatz |
| 6,126,686 A | 10/2000 | Badylak et al. |
| 6,132,438 A | 10/2000 | Fleischman et al. |
| 6,143,037 A | 11/2000 | Goldstein et al. |
| 6,152,144 A | 11/2000 | Lesh et al. |
| 6,165,183 A | 12/2000 | Kuehn et al. |
| 6,165,204 A | 12/2000 | Levinson et al. |
| 6,168,588 B1 | 1/2001 | Wilson |
| 6,171,329 B1 | 1/2001 | Shaw et al. |
| 6,174,322 B1 | 1/2001 | Schneidt |
| 6,174,330 B1 | 1/2001 | Stinson |
| 6,183,443 B1 | 2/2001 | Kratoska et al. |
| 6,183,496 B1 | 2/2001 | Urbanski |
| 6,187,039 B1 | 2/2001 | Hiles et al. |
| 6,190,353 B1 | 2/2001 | Makower et al. |
| 6,190,357 B1 | 2/2001 | Ferrari et al. |
| 6,197,016 B1 | 3/2001 | Fourkas et al. |
| 6,199,262 B1 | 3/2001 | Martin |
| 6,206,895 B1 | 3/2001 | Levinson |
| 6,206,907 B1 | 3/2001 | Marino et al. |
| 6,214,029 B1 | 4/2001 | Thill |
| 6,217,590 B1 | 4/2001 | Levinson |
| 6,221,092 B1 | 4/2001 | Koike et al. |
| 6,227,139 B1 | 5/2001 | Nguyen et al. |
| 6,228,097 B1 | 5/2001 | Levinson et al. |
| 6,231,561 B1 | 5/2001 | Frazier et al. |
| 6,245,080 B1 | 6/2001 | Levinson |
| 6,245,537 B1 | 6/2001 | Williams et al. |
| 6,258,091 B1 | 7/2001 | Sevrain et al. |
| 6,261,309 B1 | 7/2001 | Urbanski |
| 6,265,333 B1 | 7/2001 | Dzenis et al. |
| 6,270,500 B1 | 8/2001 | Lerch |
| 6,270,515 B1 * | 8/2001 | Linden et al. ............. 606/213 |
| 6,277,138 B1 | 8/2001 | Levinson et al. |
| 6,277,139 B1 | 8/2001 | Levinson et al. |
| 6,287,317 B1 | 9/2001 | Makower et al. |
| 6,290,674 B1 | 9/2001 | Roue et al. |
| 6,290,721 B1 | 9/2001 | Heath |
| 6,299,635 B1 | 10/2001 | Frantzen |
| 6,306,150 B1 | 10/2001 | Levinson |
| 6,306,424 B1 | 10/2001 | Vyakarnam et al. |
| 6,312,443 B1 | 11/2001 | Stone |
| 6,312,446 B1 | 11/2001 | Huebsch et al. |
| 6,315,791 B1 | 11/2001 | Gingras et al. |
| 6,316,262 B1 | 11/2001 | Huisman et al. |
| 6,319,263 B1 | 11/2001 | Levinson |
| 6,322,548 B1 | 11/2001 | Payne et al. |
| 6,328,727 B1 | 12/2001 | Frazier et al. |
| 6,334,872 B1 | 1/2002 | Termin et al. |
| 6,342,064 B1 | 1/2002 | Koike et al. |
| 6,344,048 B1 | 2/2002 | Chin et al. |
| 6,344,049 B1 | 2/2002 | Levinson et al. |
| 6,346,074 B1 | 2/2002 | Roth |
| 6,348,041 B1 | 2/2002 | Klint |
| 6,352,552 B1 | 3/2002 | Levinson et al. |
| 6,355,052 B1 | 3/2002 | Neuss et al. |
| 6,356,782 B1 | 3/2002 | Sirimanne et al. |
| 6,358,238 B1 | 3/2002 | Sherry |
| 6,364,853 B1 | 4/2002 | French et al. |
| 6,368,338 B1 | 4/2002 | Konya et al. |
| 6,371,904 B1 | 4/2002 | Sirimanne et al. |
| 6,375,625 B1 | 4/2002 | French et al. |
| 6,375,668 B1 | 4/2002 | Gifford et al. |
| 6,375,671 B1 | 4/2002 | Kobayashi et al. |
| 6,379,342 B1 | 4/2002 | Levinson |
| 6,379,363 B1 | 4/2002 | Herrington et al. |
| 6,379,368 B1 | 4/2002 | Corcoran et al. |
| 6,387,104 B1 | 5/2002 | Pugsley, Jr. et al. |
| 6,398,796 B2 | 6/2002 | Levinson |
| 6,402,772 B1 | 6/2002 | Amplatz et al. |
| 6,419,669 B1 | 7/2002 | Frazier et al. |
| 6,426,145 B1 | 7/2002 | Moroni |
| 6,436,088 B2 | 8/2002 | Frazier et al. |
| 6,440,152 B1 | 8/2002 | Gainor et al. |
| 6,443,972 B1 | 9/2002 | Bosma et al. |
| 6,450,987 B1 | 9/2002 | Kramer |
| 6,460,749 B1 | 10/2002 | Levinson et al. |
| 6,468,303 B1 | 10/2002 | Amplatz et al. |
| 6,478,773 B1 | 11/2002 | Gandhi et al. |
| 6,482,224 B1 | 11/2002 | Michler et al. |
| 6,488,706 B1 | 12/2002 | Solymar |
| 6,491,714 B1 | 12/2002 | Bennett |
| 6,494,846 B1 | 12/2002 | Margolis |
| 6,494,888 B1 | 12/2002 | Laufer et al. |
| 6,497,709 B1 | 12/2002 | Heath |
| 6,506,204 B2 | 1/2003 | Mazzocchi |
| 6,508,828 B1 | 1/2003 | Akerfeldt et al. |
| 6,514,515 B1 | 2/2003 | Williams |
| 6,548,569 B1 | 4/2003 | Williams et al. |
| 6,551,303 B1 | 4/2003 | Van Tassel et al. |
| 6,551,344 B2 | 4/2003 | Thill |
| 6,554,849 B1 | 4/2003 | Jones et al. |
| 6,585,719 B2 | 7/2003 | Wang |
| 6,585,755 B2 | 7/2003 | Jackson et al. |

(56) References Cited

U.S. PATENT DOCUMENTS

| | | |
|---|---|---|
| 6,589,251 B2 | 7/2003 | Yee et al. |
| 6,596,013 B2 | 7/2003 | Yang et al. |
| 6,599,448 B1 | 7/2003 | Ehrhard, Jr. et al. |
| 6,610,764 B1 | 8/2003 | Martin et al. |
| 6,623,506 B2 | 9/2003 | McGuckin et al. |
| 6,623,508 B2 | 9/2003 | Shaw et al. |
| 6,623,518 B2 | 9/2003 | Thompson et al. |
| 6,626,936 B2 | 9/2003 | Stinson |
| 6,629,901 B2 | 10/2003 | Huang |
| 6,652,556 B1 | 11/2003 | Van Tassel et al. |
| 6,666,861 B1 | 12/2003 | Grabek |
| 6,669,707 B1 | 12/2003 | Swanstrom et al. |
| 6,669,713 B2 | 12/2003 | Adams |
| 6,669,722 B2 | 12/2003 | Chen et al. |
| 6,685,707 B2 | 2/2004 | Roman et al. |
| 6,689,589 B2 | 2/2004 | Huisman et al. |
| 6,712,804 B2 | 3/2004 | Roue et al. |
| 6,712,836 B1 | 3/2004 | Berg et al. |
| 6,726,696 B1 | 4/2004 | Houser et al. |
| 6,755,834 B2 | 6/2004 | Amis |
| 6,786,915 B2 | 9/2004 | Akerfeldt et al. |
| 6,828,357 B1 | 12/2004 | Martin et al. |
| 6,838,493 B2 | 1/2005 | Williams et al. |
| 6,855,126 B2 | 2/2005 | Flinchbaugh |
| 6,860,895 B1 | 3/2005 | Akerfeldt et al. |
| 6,866,669 B2 | 3/2005 | Buzzard et al. |
| 6,867,247 B2 | 3/2005 | Williams et al. |
| 6,867,248 B1 | 3/2005 | Martin et al. |
| 6,867,249 B2 | 3/2005 | Lee |
| 6,921,401 B2 | 7/2005 | Lerch et al. |
| 6,921,410 B2 | 7/2005 | Porter |
| 6,939,352 B2 | 9/2005 | Buzzard et al. |
| 6,994,092 B2 | 2/2006 | Van Der Burg et al. |
| 7,044,134 B2 | 5/2006 | Khairkhahan et al. |
| 7,048,738 B1 | 5/2006 | Wellisz et al. |
| 7,097,653 B2 | 8/2006 | Freudenthal et al. |
| 7,128,073 B1 | 10/2006 | Van Der Burg et al. |
| 7,149,587 B2 | 12/2006 | Wardle et al. |
| 7,152,605 B2 | 12/2006 | Khairkhahan et al. |
| 7,165,552 B2 | 1/2007 | Deem et al. |
| 7,198,631 B2 | 4/2007 | Kanner et al. |
| 7,207,402 B2 | 4/2007 | Bjoerk |
| 7,223,271 B2 | 5/2007 | Muramatsu et al. |
| 7,238,188 B2 | 7/2007 | Nesper et al. |
| 7,335,426 B2 | 2/2008 | Marton et al. |
| 7,361,178 B2 | 4/2008 | Hearn et al. |
| 7,381,216 B2 | 6/2008 | Buzzard et al. |
| 7,431,729 B2 | 10/2008 | Chanduszko |
| 7,452,363 B2 | 11/2008 | Ortiz |
| 7,481,832 B1 | 1/2009 | Meridew et al. |
| 7,582,104 B2 | 9/2009 | Corcoan et al. |
| 7,597,704 B2 | 10/2009 | Frazier et al. |
| 7,658,748 B2 | 2/2010 | Marino et al. |
| 7,678,123 B2 | 3/2010 | Chanduszko |
| 7,704,268 B2 | 4/2010 | Chanduszko |
| 7,735,493 B2 | 6/2010 | van der Burg et al. |
| 7,780,700 B2 * | 8/2010 | Frazier et al. ............. 606/216 |
| 7,842,053 B2 * | 11/2010 | Chanduszko et al. ....... 606/157 |
| 7,871,419 B2 | 1/2011 | Devellian |
| 7,875,052 B2 | 1/2011 | Kawaura et al. |
| 7,887,562 B2 | 2/2011 | Young et al. |
| 7,905,901 B2 | 3/2011 | Corcoan et al. |
| 7,918,872 B2 | 4/2011 | Mitelberg et al. |
| 8,034,061 B2 | 10/2011 | Amplatz et al. |
| 8,062,325 B2 | 11/2011 | Mitelberg et al. |
| 8,118,833 B2 | 2/2012 | Seibold et al. |
| 8,257,389 B2 | 9/2012 | Chanduszko et al. |
| 8,277,480 B2 | 10/2012 | Callaghan et al. |
| 8,308,760 B2 | 11/2012 | Chanduszko |
| 8,361,110 B2 * | 1/2013 | Chanduszko ............... 606/213 |
| 8,480,706 B2 | 7/2013 | Chanduszko et al. |
| 8,551,135 B2 | 10/2013 | Kladakis et al. |
| 8,753,362 B2 | 6/2014 | Widomski et al. |
| 8,764,790 B2 | 7/2014 | Thommen et al. |
| 8,764,848 B2 | 7/2014 | Callaghan et al. |
| 8,821,528 B2 | 9/2014 | McGuckin et al. |
| 8,858,576 B2 | 10/2014 | Takahashi et al. |
| 9,005,242 B2 | 4/2015 | Cahill |
| 9,119,607 B2 | 9/2015 | Amin |
| 9,138,213 B2 | 9/2015 | Amin et al. |
| 9,326,759 B2 | 5/2016 | Chanduszko et al. |
| 2001/0010481 A1 | 8/2001 | Blanc et al. |
| 2001/0014800 A1 | 8/2001 | Frazier et al. |
| 2001/0025132 A1 | 9/2001 | Alferness et al. |
| 2001/0034537 A1 | 10/2001 | Shaw et al. |
| 2001/0034567 A1 | 10/2001 | Allen et al. |
| 2001/0037129 A1 | 11/2001 | Thill |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0044639 A1 | 11/2001 | Levinson |
| 2001/0049492 A1 | 12/2001 | Frazier et al. |
| 2001/0049551 A1 | 12/2001 | Tseng et al. |
| 2002/0010481 A1 | 1/2002 | Jayaraman |
| 2002/0019648 A1 | 2/2002 | Akerfeldt et al. |
| 2002/0022859 A1 | 2/2002 | Hogendijk |
| 2002/0022860 A1 | 2/2002 | Borillo et al. |
| 2002/0026208 A1 | 2/2002 | Roe et al. |
| 2002/0029048 A1 | 3/2002 | Miller |
| 2002/0032459 A1 | 3/2002 | Horzewski et al. |
| 2002/0032462 A1 | 3/2002 | Houser et al. |
| 2002/0034259 A1 | 3/2002 | Tada |
| 2002/0035374 A1 | 3/2002 | Borillo et al. |
| 2002/0043307 A1 | 4/2002 | Ishida et al. |
| 2002/0049457 A1 | 4/2002 | Kaplan et al. |
| 2002/0052572 A1 | 5/2002 | Franco et al. |
| 2002/0058980 A1 | 5/2002 | Sass |
| 2002/0058989 A1 | 5/2002 | Chen et al. |
| 2002/0077555 A1 | 6/2002 | Schwartz |
| 2002/0095174 A1 | 7/2002 | Tsugita et al. |
| 2002/0096183 A1 | 7/2002 | Stevens et al. |
| 2002/0099389 A1 | 7/2002 | Michler et al. |
| 2002/0099390 A1 | 7/2002 | Kaplan et al. |
| 2002/0099437 A1 | 7/2002 | Anson et al. |
| 2002/0103492 A1 | 8/2002 | Kaplan et al. |
| 2002/0107531 A1 | 8/2002 | Schreck et al. |
| 2002/0111537 A1 | 8/2002 | Taylor et al. |
| 2002/0111637 A1 | 8/2002 | Kaplan et al. |
| 2002/0111647 A1 | 8/2002 | Khairkhahan et al. |
| 2002/0120323 A1 | 8/2002 | Thompson et al. |
| 2002/0128680 A1 | 9/2002 | Pavlovic |
| 2002/0129819 A1 | 9/2002 | Feldman et al. |
| 2002/0143292 A1 | 10/2002 | Flinchbaugh |
| 2002/0156475 A1 | 10/2002 | Lerch et al. |
| 2002/0156499 A1 | 10/2002 | Konya et al. |
| 2002/0164729 A1 | 11/2002 | Skraly et al. |
| 2002/0169377 A1 | 11/2002 | Khairkhahan et al. |
| 2002/0183786 A1 | 12/2002 | Girton |
| 2002/0183787 A1 | 12/2002 | Wahr et al. |
| 2002/0183823 A1 | 12/2002 | Pappu |
| 2002/0198563 A1 | 12/2002 | Gainor et al. |
| 2003/0004533 A1 | 1/2003 | Dieck et al. |
| 2003/0023266 A1 | 1/2003 | Welch et al. |
| 2003/0028213 A1 | 2/2003 | Thill et al. |
| 2003/0045893 A1 | 3/2003 | Ginn |
| 2003/0050665 A1 | 3/2003 | Ginn |
| 2003/0055455 A1 | 3/2003 | Yang et al. |
| 2003/0057156 A1 | 3/2003 | Peterson et al. |
| 2003/0059640 A1 | 3/2003 | Marton et al. |
| 2003/0065379 A1 | 4/2003 | Babbs et al. |
| 2003/0100920 A1 | 5/2003 | Akin et al. |
| 2003/0113868 A1 | 6/2003 | Flor et al. |
| 2003/0120337 A1 | 6/2003 | Van Tassel et al. |
| 2003/0130683 A1 | 7/2003 | Andreas et al. |
| 2003/0139819 A1 | 7/2003 | Beer et al. |
| 2003/0150821 A1 | 8/2003 | Bates et al. |
| 2003/0171774 A1 | 9/2003 | Freudenthal et al. |
| 2003/0187390 A1 | 10/2003 | Bates et al. |
| 2003/0191495 A1 | 10/2003 | Ryan et al. |
| 2003/0195530 A1 | 10/2003 | Thill |
| 2003/0195555 A1 | 10/2003 | Khairkhahan et al. |
| 2003/0204203 A1 | 10/2003 | Khairkhahan et al. |
| 2003/0225421 A1 | 12/2003 | Peavey et al. |

(56) References Cited

U.S. PATENT DOCUMENTS

| | | |
|---|---|---|
| 2003/0225439 A1 | 12/2003 | Cook et al. |
| 2004/0006330 A1 | 1/2004 | Fangrow |
| 2004/0044361 A1 | 3/2004 | Frazier et al. |
| 2004/0044364 A1 | 3/2004 | DeVries et al. |
| 2004/0073242 A1 | 4/2004 | Chanduszko |
| 2004/0098042 A1 | 5/2004 | Devellian et al. |
| 2004/0116959 A1 | 6/2004 | McGuckin et al. |
| 2004/0127919 A1 | 7/2004 | Trout et al. |
| 2004/0133230 A1 | 7/2004 | Carpenter et al. |
| 2004/0133236 A1 | 7/2004 | Chanduszko |
| 2004/0143294 A1 | 7/2004 | Corcoran et al. |
| 2004/0167566 A1 | 8/2004 | Beulke et al. |
| 2004/0176799 A1 | 9/2004 | Chanduszko et al. |
| 2004/0186510 A1 | 9/2004 | Weaver |
| 2004/0210301 A1 | 10/2004 | Obermiller |
| 2004/0220596 A1* | 11/2004 | Frazier ............... A61B 17/0057 606/153 |
| 2004/0220610 A1 | 11/2004 | Kreidler et al. |
| 2004/0230222 A1 | 11/2004 | van der Burg et al. |
| 2004/0234567 A1 | 11/2004 | Dawson |
| 2004/0254594 A1 | 12/2004 | Alfaro |
| 2005/0025809 A1 | 2/2005 | Hasirci et al. |
| 2005/0038470 A1 | 2/2005 | Van Der Burg et al. |
| 2005/0043759 A1 | 2/2005 | Chanduszko |
| 2005/0055039 A1 | 3/2005 | Burnett et al. |
| 2005/0065548 A1 | 3/2005 | Marino et al. |
| 2005/0070935 A1 | 3/2005 | Ortiz |
| 2005/0080476 A1 | 4/2005 | Gunderson et al. |
| 2005/0113868 A1 | 5/2005 | Devellian |
| 2005/0119690 A1 | 6/2005 | Mazzocchi et al. |
| 2005/0182426 A1 | 8/2005 | Adams et al. |
| 2005/0187564 A1 | 8/2005 | Jayaraman |
| 2005/0187568 A1 | 8/2005 | Klenk et al. |
| 2005/0192626 A1 | 9/2005 | Widomski et al. |
| 2005/0192627 A1 | 9/2005 | Whisenant et al. |
| 2005/0267523 A1 | 12/2005 | Devellian et al. |
| 2005/0267525 A1 | 12/2005 | Chanduszko |
| 2005/0267572 A1 | 12/2005 | Schoon et al. |
| 2005/0273135 A1 | 12/2005 | Chanduszko et al. |
| 2005/0288706 A1 | 12/2005 | Widomski et al. |
| 2005/0288786 A1 | 12/2005 | Chanduszko |
| 2006/0020332 A1* | 1/2006 | Lashinski et al. ............ 623/2.11 |
| 2006/0025790 A1 | 2/2006 | de Winter et al. |
| 2006/0030884 A1 | 2/2006 | Yeung et al. |
| 2006/0106447 A1 | 5/2006 | Opolski |
| 2006/0109073 A1* | 5/2006 | Allison et al. .................. 337/66 |
| 2006/0116710 A1 | 6/2006 | Corcoran et al. |
| 2006/0122646 A1 | 6/2006 | Corcoran et al. |
| 2006/0122647 A1 | 6/2006 | Callaghan et al. |
| 2006/0167494 A1 | 7/2006 | Suddaby |
| 2006/0206148 A1 | 9/2006 | Khairkhahan et al. |
| 2006/0217764 A1 | 9/2006 | Abbott et al. |
| 2006/0224183 A1 | 10/2006 | Freudenthal |
| 2006/0235463 A1 | 10/2006 | Freudenthal et al. |
| 2006/0241690 A1 | 10/2006 | Amplatz et al. |
| 2006/0265004 A1 | 11/2006 | Callaghan et al. |
| 2006/0271089 A1 | 11/2006 | Alejandro et al. |
| 2006/0276839 A1 | 12/2006 | McGuckin |
| 2007/0010851 A1 | 1/2007 | Chanduszko et al. |
| 2007/0066994 A1 | 3/2007 | Blaeser et al. |
| 2007/0112381 A1 | 5/2007 | Figulla et al. |
| 2007/0118176 A1 | 5/2007 | Opolski et al. |
| 2007/0129755 A1 | 6/2007 | Abbott et al. |
| 2007/0167981 A1 | 7/2007 | Opolski |
| 2007/0179474 A1 | 8/2007 | Cahill et al. |
| 2007/0185529 A1 | 8/2007 | Coleman et al. |
| 2007/0191884 A1 | 8/2007 | Eskridge et al. |
| 2007/0225760 A1 | 9/2007 | Moszner et al. |
| 2007/0244517 A1 | 10/2007 | Callaghan |
| 2007/0244518 A1 | 10/2007 | Callaghan |
| 2007/0250081 A1 | 10/2007 | Cahill et al. |
| 2007/0250115 A1 | 10/2007 | Opolski et al. |
| 2007/0265656 A1* | 11/2007 | Amplatz et al. ............. 606/200 |
| 2007/0276415 A1 | 11/2007 | Kladakis et al. |
| 2007/0282430 A1 | 12/2007 | Thommen et al. |
| 2008/0015633 A1 | 1/2008 | Abbott et al. |
| 2008/0058800 A1* | 3/2008 | Collins et al. .................. 606/41 |
| 2008/0065149 A1 | 3/2008 | Thielen et al. |
| 2008/0077180 A1 | 3/2008 | Kladakis et al. |
| 2008/0086168 A1 | 4/2008 | Cahill et al. |
| 2008/0091234 A1 | 4/2008 | Kladakis et al. |
| 2008/0109073 A1* | 5/2008 | Lashinski et al. ............. 623/2.1 |
| 2008/0119886 A1 | 5/2008 | Greenhalgh et al. |
| 2008/0119891 A1 | 5/2008 | Miles et al. |
| 2008/0147111 A1 | 6/2008 | Johnson et al. |
| 2008/0208214 A1 | 8/2008 | Sato et al. |
| 2008/0228218 A1 | 9/2008 | Chanduszko |
| 2008/0249562 A1 | 10/2008 | Cahill |
| 2008/0262518 A1 | 10/2008 | Freudenthal |
| 2009/0012559 A1 | 1/2009 | Chanduszko |
| 2009/0054912 A1 | 2/2009 | Heanue et al. |
| 2009/0062844 A1 | 3/2009 | Tekulve et al. |
| 2009/0069885 A1 | 3/2009 | Rahdert et al. |
| 2009/0076541 A1 | 3/2009 | Chin et al. |
| 2009/0088795 A1 | 4/2009 | Cahill |
| 2009/0118745 A1* | 5/2009 | Paul, Jr. ............. A61B 17/0057 606/151 |
| 2009/0204133 A1 | 8/2009 | Melzer et al. |
| 2009/0228038 A1* | 9/2009 | Amin ................ A61B 17/0057 606/213 |
| 2009/0292310 A1 | 11/2009 | Chin et al. |
| 2009/0306706 A1 | 12/2009 | Osypka |
| 2010/0004679 A1 | 1/2010 | Osypka |
| 2010/0121370 A1 | 5/2010 | Kariniemi |
| 2010/0145385 A1 | 6/2010 | Surti et al. |
| 2010/0234878 A1 | 9/2010 | Hruska et al. |
| 2010/0234884 A1* | 9/2010 | Lafontaine et al. ........... 606/213 |
| 2010/0234885 A1 | 9/2010 | Frazier et al. |
| 2010/0324538 A1 | 12/2010 | Van Orden |
| 2010/0324585 A1 | 12/2010 | Miles et al. |
| 2010/0324652 A1 | 12/2010 | Aurilia et al. |
| 2011/0040324 A1* | 2/2011 | McCarthy et al. ........... 606/215 |
| 2011/0054519 A1 | 3/2011 | Neuss |
| 2011/0184439 A1 | 7/2011 | Anderson et al. |
| 2011/0184456 A1 | 7/2011 | Grandfield et al. |
| 2011/0295298 A1 | 12/2011 | Moszner |
| 2011/0301630 A1 | 12/2011 | Hendriksen et al. |
| 2012/0029556 A1 | 2/2012 | Masters |
| 2012/0071918 A1 | 3/2012 | Amin et al. |
| 2012/0143242 A1 | 6/2012 | Masters |
| 2012/0150218 A1 | 6/2012 | Sandgren et al. |
| 2012/0197292 A1 | 8/2012 | Chin-Chen et al. |
| 2012/0245623 A1 | 9/2012 | Kariniemi et al. |
| 2012/0316597 A1 | 12/2012 | Fitz et al. |
| 2013/0218202 A1 | 8/2013 | Masters |
| 2013/0231684 A1 | 9/2013 | Aurilia et al. |
| 2013/0245666 A1 | 9/2013 | Larsen et al. |
| 2013/0282054 A1 | 10/2013 | Osypka |
| 2013/0296925 A1 | 11/2013 | Chanduszko et al. |
| 2014/0039543 A1 | 2/2014 | Willems et al. |
| 2014/0142610 A1 | 5/2014 | Larsen et al. |
| 2014/0194921 A1 | 7/2014 | Akpinar |
| 2014/0207185 A1 | 7/2014 | Goble et al. |
| 2014/0309684 A1 | 10/2014 | Al-Qbandi et al. |
| 2014/0343602 A1 | 11/2014 | Cox et al. |
| 2015/0005809 A1 | 1/2015 | Ayres et al. |
| 2015/0039023 A1 | 2/2015 | Canniere et al. |
| 2015/0066077 A1 | 3/2015 | Akpinar |
| 2015/0148731 A1 | 5/2015 | McNamara et al. |
| 2015/0196288 A1 | 7/2015 | Van Orden |
| 2017/0035435 A1 | 2/2017 | Amin et al. |

FOREIGN PATENT DOCUMENTS

| | | |
|---|---|---|
| DE | 9413645 U1 | 10/1994 |
| DE | 9413649 U1 | 10/1994 |
| DE | 102006036649 A1 | 10/2007 |
| EP | 200362113 A1 | 4/1990 |
| EP | 200474887 A1 | 3/1992 |
| EP | 0839549 A1 | 5/1998 |
| EP | 1013227 A2 | 6/1998 |
| EP | 3861632 A1 | 9/1998 |
| EP | 1046375 A1 | 10/2000 |
| EP | 1222897 A2 | 7/2002 |

(56) References Cited

FOREIGN PATENT DOCUMENTS

| | | |
|---|---|---|
| EP | 2340770 A1 | 7/2011 |
| EP | 2524653 A1 | 11/2012 |
| JP | 2006013686 | 4/1994 |
| JP | 2000505668 A | 5/2000 |
| JP | 2000300571 A | 10/2000 |
| JP | 2004534390 A | 11/2004 |
| JP | 2005521447 A | 7/2005 |
| JP | 2005521818 A | 7/2005 |
| JP | 2005261597 | 9/2005 |
| JP | 2006230800 A | 9/2006 |
| JP | 2009160402 A | 7/2009 |
| JP | 2010244611 | 10/2010 |
| RU | 2208400 C2 | 7/2003 |
| RU | 84711 U1 | 7/2009 |
| SU | 1377052 A1 | 2/1988 |
| WO | WO9319803 A1 | 10/1993 |
| WO | WO9601591 A1 | 1/1996 |
| WO | WO9625179 A1 | 8/1996 |
| WO | WO9631157 A1 | 10/1996 |
| WO | WO9640305 | 12/1996 |
| WO | WO9807375 A1 | 2/1998 |
| WO | WO9808462 A2 | 3/1998 |
| WO | WO9816174 A1 | 4/1998 |
| WO | WO9829026 A2 | 7/1998 |
| WO | WO9851812 A2 | 11/1998 |
| WO | WO9905977 A1 | 2/1999 |
| WO | WO9818864 | 4/1999 |
| WO | WO9918862 A1 | 4/1999 |
| WO | WO9918864 A1 | 4/1999 |
| WO | WO9918870 A1 | 4/1999 |
| WO | WO9918871 A1 | 4/1999 |
| WO | WO9930640 A1 | 6/1999 |
| WO | WO9939646 A1 | 8/1999 |
| WO | WO9966846 A1 | 12/1999 |
| WO | WO0027292 A1 | 5/2000 |
| WO | WO0044428 A2 | 8/2000 |
| WO | WO0051500 A1 | 9/2000 |
| WO | WO0108600 A2 | 2/2001 |
| WO | WO0119256 A1 | 2/2001 |
| WO | WO0117435 A1 | 3/2001 |
| WO | WO0121247 A1 | 3/2001 |
| WO | WO0128432 A1 | 4/2001 |
| WO | WO0130268 A1 | 5/2001 |
| WO | WO0149185 A1 | 7/2001 |
| WO | WO0172367 A1 | 10/2001 |
| WO | WO0178596 A1 | 10/2001 |
| WO | WO0193783 A2 | 12/2001 |
| WO | WO0217809 A1 | 3/2002 |
| WO | WO0224106 A2 | 3/2002 |
| WO | WO0238051 A2 | 5/2002 |
| WO | WO03001893 | 1/2003 |
| WO | WO03024337 A1 | 3/2003 |
| WO | WO03053493 A2 | 7/2003 |
| WO | WO03059152 A2 | 7/2003 |
| WO | WO03061481 A1 | 7/2003 |
| WO | WO03063732 A2 | 8/2003 |
| WO | WO03077733 A2 | 9/2003 |
| WO | WO03082076 A2 | 10/2003 |
| WO | 03103476 A2 | 12/2003 |
| WO | WO03103476 A2 | 12/2003 |
| WO | WO2004012603 A2 | 2/2004 |
| WO | WO2004032993 A2 | 4/2004 |
| WO | WO2004037333 A1 | 5/2004 |
| WO | WO2004043266 A2 | 5/2004 |
| WO | WO2004043508 A1 | 5/2004 |
| WO | WO2004052213 A1 | 6/2004 |
| WO | WO2004067092 A2 | 8/2004 |
| WO | WO2004101019 A2 | 11/2004 |
| WO | WO2005006990 A2 | 1/2005 |
| WO | WO2005018728 A2 | 3/2005 |
| WO | WO2005027752 A1 | 3/2005 |
| WO | WO2005032335 A2 | 4/2005 |
| WO | WO2005034724 A2 | 4/2005 |
| WO | WO2005074813 A1 | 8/2005 |
| WO | WO2005092203 A1 | 10/2005 |
| WO | WO2005110240 A1 | 11/2005 |
| WO | WO2005112779 A1 | 12/2005 |
| WO | WO2006036837 A2 | 4/2006 |
| WO | WO2006041612 A2 | 4/2006 |
| WO | WO2006062711 A2 | 6/2006 |
| WO | WO2006102213 A1 | 9/2006 |
| WO | WO2007124862 A2 | 11/2007 |
| WO | WO2007140797 A1 | 12/2007 |
| WO | WO2007140797 A1 | 12/2007 |
| WO | WO2008125689 A1 | 10/2008 |
| WO | WO2008125689 A1 | 10/2008 |
| WO | WO2008137603 A2 | 11/2008 |
| WO | WO2008153872 A2 | 12/2008 |
| WO | WO2008156464 A1 | 12/2008 |
| WO | WO2012003317 A1 | 1/2012 |
| WO | WO2012003317 A1 | 1/2012 |

OTHER PUBLICATIONS

Athanasion, "Coronary artery bypass with the use of a magnetic distal anastomotic device: surgical technique and preliminary experience," Heart Surg Forum., 2004;7(6):356-359.

Bachthaler, M. et al., "Corrosion of Tungsten Coils After Peripheral Vascular Embolization Theraphy: Influence on Outcome and Tungsten Load", Catherization and Cardiovascular Interventions, vol. 62, pp. 380-384, 2004.

Chinese Search Report in Application No. 200980158768.9, dated Jun. 16, 2013, 4 pages.

European Examination Report, European Application No. 03729663.9, mailed Jul. 16, 2008 (5 Pages).

European Examination Report, European Application No. 03731562.9, mailed Jul. 18, 2008 (3 Pages).

European Examination Report, European Application No. 03779297.5, mailed Mar. 15, 2007 (6 Pages).

European Examination Report, European Application No. 04781644.2, mailed Aug. 23, 2007 (3 Pages).

European Search Report, European Application No. 03729663.9, mailed Feb. 20, 2008 (3 Pages).

European Search Report, European Application No. 11007412.7, mailed Jan. 19, 2012, 5 pages.

Falk, V., "Facilitated Endoscopic Beating Heart Coronary Artery Bypass Grafting Using a Magentic Coupling Device," Journal of Thoracic and Cardiovascular Surgery, vol. 126,(5), pp. 1575-1579.

Filsoufi, F., et al., "Automated Distal Coronary Bypass with a Novel Magnetic Coupler (MVP system)," J. Thoracic and Cardiovascular Surgery, vol. 127(1), pp. 185-192.

International Preliminary Report on Patentability and Written Opinion for PCT/US2010/039354 issued Jan. 4, 2012, 5 pages.

International Preliminary Report on Patentability and Written Opinion for PCT/US2010/039358 issued Jan. 4, 2012, 7 pages.

International Preliminary Report on Patentability and Written Opinion for PCT/US2009/004307, mailed Sep. 13, 2011, 8 pages.

International Preliminary Report on Patentability for PCT/US2012/063598, issued May 13, 2014, 7 pages.

International Search Report and Written Opinion for PCT/US2012/063598, mailed Feb. 4, 2013, 11 pages.

International Search Report and Written Opinion for PCT/US2014/011980, mailed Sep. 9, 2014, 32 pages.

International Search Report and Written Opinion for PCT/US2014/017129 mailed May 14, 2014, 9 pages.

International Search Report and Written Opinion, International Patent Application No. PCT/US06/41255, mailed Jun. 13, 2008 (6 pgs).

International Search Report and Written Opinion, International Patent Application No. PCT/US08/59429, mailed Sep. 5, 2008 (9 pgs).

International Search Report for International Patent Application No. PCT/AU03/00759, filed Jun. 19, 2003.

International Search Report for PCT/US2009/004307, mailed Nov. 27, 2009, 6 pages.

International Search Report for PCT/US2010/039354, mailed Sep. 15, 2010, 5 pages.

(56) References Cited

OTHER PUBLICATIONS

International Search Report for PCT/US2010/039358 mailed Sep. 3, 2010, 5 pages.
International Search Report for PCT/US2012/050785, mailed Nov. 23, 2012, 6 pages.
International Search Report, International Application No. PCT/US02/40850 mailed Jun. 19, 2003 (4 pgs).
International Search Report, International Application No. PCT/US03/01050, mailed Jul. 8, 2003 (1 pg).
International Search Report, International Application No. PCT/US03/09051, mailed Sep. 29, 2003 (2 pgs).
International Search Report, International Application No. PCT/US03/17390, mailed Oct. 6, 2003 (2 pgs).
International Search Report, International Application No. PCT/US03/17715, mailed Mar. 24, 2004 (2 pgs).
International Search Report, International Application No. PCT/US03/32133, mailed Apr. 22, 2004 (1 pg).
International Search Report, International Application No. PCT/US03/34003 mailed Oct. 3, 2004 (4 pgs).
International Search Report, International Application No. PCT/US03/35479, mailed Apr. 14, 2004 (2 pgs).
International Search Report, International Application No. PCT/US03/35998 mailed Jun. 16, 2004 (5 pgs}.
International Search Report, International Application No. PCT/US03/39253, mailed Apr. 19, 2004 (4 pgs).
International Search Report, International Application No. PCT/US04/022643, mailed Mar. 31, 2005 (2 pgs).
International Search Report, International Application No. PCT/US04/026998, mailed Apr. 22, 2005 (5 pqs}.
International Search Report, International Application No. PCT/US04/029978, mailed Jan. 26, 2005 (3 pgs).
International Search Report, International Application No. PCT/US05/015382, mailed Oct. 6, 2005 (4 pgs).
International Search Report, International Application No. PCT/US05/34276, mailed Oct. 9, 2007.
International Search Report, International Application No. PCT/US06/009978, mailed Jul. 13, 2006 (2 pgs).
International Search Report, International Application No. PCT/US07/065546, mailed Oct. 29, 2007. 2 pages.
International Search Report, International Application No. PCT/US2007/065526, mailed Aug. 8, 2007 (5 pgs).
International Search Report, International Application No. PCT/US2007/065541, mailed Aug. 7, 2007 (4 pgs).
International Search Report, International Application No. PCT/US97/14822, mailed Feb. 20, 1998 (2 pgs).
International Search Report, International Application No. PCT/US97/17927, mailed Feb. 10, 1998 (1 pg).
International Search Report, International Application No. PCT/USO5/006703, mailed Jul. 25, 2005 1(3 pgs).
International Search Report, International Application No. PCT/USO5/013705 mailed Aug. 4, 2005 (4 pgs).
Isotalo, T. et al., "Biocompatibility Testing of a New Bioabsorbable X-Ray Positive SR-PLA 96/4 Urethral Stent", The Journal of Uroloav. vol. 163, pp. 1764-1767, Nov. 1999.
Jackson et al., "55-nitinol-the alloy with a memory—its physical metallurgy, properties and applications," NASA, pp. 24-25, 1972.
Klima, U., "Magnetic Vascular Port in Minimally Invasive Direct Coronary Artery Bypass Grafting," Circulation, 2004, 11-55-11-60.
Meier and Lock, "Contemporary management of patent foramen ovale," Circulation., Jan. 7, 2003;107(1):5-9.
Parviainen, M. et al., "A New Biodegradable Stent for the Pancreaticojejunal Anastomosis After Pancreaticoduodenal Resection: In Vitro Examination and Pilot Experiences in Humans", Pancreas, vol. 21, No. 1, pp. 14-21, 2000.
Ramanathan, G., et. al., "Experimental and Computational Methods for Shape Memory Alloys," 15th ASCE Engineering Mechanics Conference, Jun. 2-5, 2002.
Ruddy, A. C. et al., "Rheological, Mechanical and Thermal Behaviour of Radipaque Filled Polymers", Polymer Processing Research Centre, School of Chemical Engineering, Queen's University of Belfast , 5 pages.
Ruiz, et al., "The puncture technique: A new method for transcatheter closure of patent foramen ovale," Catheterization and Cardiovascular Interventions, 2001, vol. 53, pp. 369-372.
Schaffer and Gordon, "Engineering Characteristics of Drawn Filled Nitinol Tube" SMST-2003: Proceedings of the International Conference on Shape Memory and Superelastic Technologies (ASM International), pp. 109-118, 2004.
Shabalovskaya, "Surface, corrosion and biocompatibility aspects of Nitinol as an implant material," Biomed Mater Eng., 2002;12(1):69-109.
Stein, H., "Telemanipulator-gestutzte Applikation eines magnetischen Gefäss-Kopplers am schlagenden Herzen mit dem da Vinci' -Surgical-System," Biomedizinische Technik, 2003, vol. 48 (9), pp. 230-234.
Stockel, "Nitinol Medical Devices and Implants," Min Invas Ther & Allied Technol 9(2), Cordis Corporation—Nitino/ Devices and Components, Fremont, CA, USA, 2000pp. 81-88.
Uchil, "Shape Memory Alloys—Characterization Techniques," Pramana—Journal of Phvsics, 2002 vol. 58 (5)(6), pp. 1131-1139.
Vaajanen et al., "Expansion and fixation properties of a new braided biodegradable urethral stent: an experimental study in the rabbit," The Journal of Urology, J Urol., Mar. 2003;169(3):1171-1174.
Kimura, A., et al., "Effects of Neutron Irradiation on the Transformation Behavior in Ti—Ni Alloys," Abstract, Proceedings of the Int'l Conf. on Mariensitic Transformations, 1992, pp. 935-940.

* cited by examiner

HEART OCCLUSION DEVICES

CROSS-REFERENCE TO RELATED APPLICATIONS

This application claims priority under 35 U.S.C. §119(e) to provisional U.S. Patent Application 61/523,175, filed on Aug. 12, 2011, the entire contents of which are hereby incorporated by reference.

TECHNICAL FIELD

The present disclosure generally relates to medical devices, and more particularly relates to devices for occluding apertures in tissues and vessels.

BACKGROUND

Heart occlusion devices are used in the medical field for correcting congenital heart defects, such as atrial septal defects ("ASD"), patent foramen ovale ("PFO") defects, ventricular septal defects ("VSD"), and patent ductus arteriosus ("PDA") defects. A PFO, illustrated in FIG. 1 at 110, is a persistent, one-way, usually flap-like opening in the wall between the right atrium 102 and left atrium 104 of the heart 100. The foramen ovale 110 serves a desired purpose when a fetus is gestating in utero. Because blood is oxygenated through the umbilical cord and not through the developing lungs, the circulatory system of the fetal heart allows the blood to flow through the foramen ovale as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two over-lapping layers of tissue: septum primum 118 and septum secundum 120.

However, a PFO has been shown to persist in a number of adults. Because left atrial (LA) pressure is normally higher than right atrial (RA) pressure, the flap usually stays closed. Under certain conditions, however, right atrial pressure can exceed left atrial pressure, creating the possibility that blood could pass from the right atrium 102 to the left atrium 104, and blood clots could enter the systemic circulation. It is desirable that this circumstance be eliminated.

The presence of a PFO defect is generally considered to have no therapeutic consequence in otherwise healthy adults. Paradoxical embolism via a PFO defect is considered in the diagnosis for patients who have suffered a stroke or transient ischemic attack (TIA) in the presence of a PFO and without another identified cause of ischemic stroke. While there is currently no definitive proof of a cause-effect relationship, many studies have confirmed a strong association between the presence of a PFO defect and the risk for paradoxical embolism or stroke. In addition, there is significant evidence that patients with a PFO defect who have had a cerebral vascular event are at increased risk for future, recurrent cerebrovascular events.

Accordingly, patients at such an increased risk are considered for prophylactic medical therapy to reduce the risk of a recurrent embolic event. These patients are commonly treated with oral anticoagulants, which potentially have adverse side effects, such as hemorrhaging, hematoma, and interactions with a variety of other drugs. The use of these drugs can alter a person's recovery and necessitate adjustments in a person's daily living pattern.

In certain cases, such as when anticoagulation is contraindicated, surgery may be necessary or desirable to close a PFO defect. The surgery would typically include suturing a PFO closed by attaching septum secundum to septum primum. This sutured attachment can be accomplished using either an interrupted or a continuous stitch and is a common way a surgeon shuts a PFO under direct visualization.

Umbrella devices and a variety of other similar mechanical closure devices, developed initially for percutaneous closure of atrial septal defects (ASDs), have been used in some instances to close PFOs. These devices potentially allow patients to avoid or lessen the side effects often associated with anticoagulation therapies and the risks of invasive surgery. However, umbrella devices and the like that are designed for ASDs may not be optimally suited for use as PFO closure devices.

Certain currently available septal closure devices present possible drawbacks, including technically complex implantation procedures. Additionally, complications are possible due to thrombus, fractures of the components, conduction system disturbances, perforations of heart tissue, and residual leaks. Certain devices have a high septal profile and include large masses of foreign material, which may lead to unfavorable body adaptation of a device. Given that ASD devices are designed to occlude holes, certain of such devices lack anatomic conformability to the flap-like anatomy of PFOs. The flap-like opening of the PFO is complex, and devices with a central post or devices that are self-centering may not close the defect completely, an outcome that is highly desired when closing a PFO defect. Hence, a device with a waist which can conform to the defect will have much higher chance of completely closing the defect. Even if an occlusive seal is formed, the device may be deployed in the heart on an angle, leaving some components insecurely seated against the septum and, thereby, risking thrombus formation due to hemodynamic disturbances. Finally, some septal closure devices are complex to manufacture, which may result in inconsistent product performance.

Certain devices for occluding other heart defects, e.g., ASD, VSD, PDA, also have potential drawbacks. For example, certain currently available devices tend to be either self-centering or non-self-centering and may not properly conform to the intra-cardiac anatomy. Both of these characteristics have distinct advantages and disadvantages. The non-self-centering device may not close the defect completely and may need to be over-sized significantly. This type of device may not be available for larger defects. Further, the self-centering device, if not sized properly, may cause injury to the heart. Some devices have sharp edges, which may damage the heart causing potential clinical problems. Some devices contain too much nitinol/metal, which may cause an undesired reaction in the patient. Some currently marketed devices have numerous model numbers (several available sizes), making it difficult and uneconomical for hospitals and markets to invest in starting a congenital and structural heart interventional program. The present disclosure is designed to address these and other deficiencies of certain existing closure devices.

Devices are also used for occluding other apertures, including uses such as occluding the lumen of a vessel and occluding apertures in vessel walls.

Accordingly, it is desirable to provide improved devices for occluding apertures in tissues or vessels. Furthermore, other desirable features and characteristics of the present invention will become apparent from the subsequent detailed description and the appended claims, taken in conjunction with the accompanying drawings and this background

SUMMARY

In accordance with an exemplary embodiment, a device for occluding an aperture in a tissue or vessel is provided. The device comprises a first flexible wire and a second flexible wire. Each of the first and second wires is comprised of a shape memory material. Each of the first and second wires is shaped into first and second geometric forms separated by a waist formed from two portions of the first wire and two portions of the second wire. The first geometric form of the first wire and the first geometric form of the second wire form a first plate in a first plane. The second geometric form of the first wire and the second geometric form of the second wire form a second plate in a second plane that is parallel to and remote from the first plane. The first plane has a first quadrant, a second quadrant that is adjacent to the first quadrant, a third quadrant that is below the first quadrant, and a fourth quadrant that is below the second quadrant and adjacent to the third quadrant. The second plane has a first quadrant, a second quadrant that is adjacent to the first quadrant, a third quadrant that is below the first quadrant, and a fourth quadrant that is below the second quadrant and adjacent to the third quadrant. The first quadrant of the first plane is closer to the first quadrant of the second plane than to the second, third, or fourth quadrants of the second plane. The second quadrant of the first plane is closer to the second quadrant of the second plane than to the first, third, or fourth quadrants of the second plane. The third quadrant of the first plane is closer to the third quadrant of the second plane than to the first, second, or fourth quadrants of the second plane. The fourth quadrant of the first plane is closer to the fourth quadrant of the second plane than to the first, second, or third quadrants of the second plane. The first geometric form of the first wire extends through the first and second quadrants of the first plane. The second geometric form of the first wire extends through the third and fourth quadrants of the second plane. The first geometric form of the second wire extends through the third and fourth quadrants of the first plane. The second geometric form of the second wire extends through the first and second quadrants of the second plane.

In accordance with an exemplary embodiment, a device for occluding an aperture in a tissue or vessel is provided. The device comprises a first flexible wire and a second flexible wire. Each of the first and second wires is comprised of a shape memory material. Each of the first and second wires is shaped into first and second geometric forms separated by a waist formed from two portions of the first wire and two portions of the second wire. The first geometric form of the first wire and the first geometric form of the second wire form a first plate in a first plane. The second geometric form of the first wire and the second geometric form of the second wire form a second plate in a second plane that is parallel to and remote from the first plane. The first plane has a first half-plane and a second half-plane. The second half-plane is adjacent to the first half-plane. The second plane has a third half-plane and a fourth half-plane. The third half-plane is parallel to the first half-plane. The fourth half-plane is parallel to the second half-plane and adjacent to the third half-plane. The first geometric form of the first wire is disposed in the first half-plane. The second geometric form of the first wire is disposed in the fourth half-plane. The first geometric form of the second wire is disposed in the second half-plane. The second geometric form of the second wire is disposed in the third half-plane.

In accordance with an exemplary embodiment, a device for occluding an aperture in a tissue or vessel is provided. The device comprises a first flexible wire and a second flexible wire. Each of the first and second wires is comprised of a shape memory material. Each of the first and second wires is shaped into first and second geometric forms separated by a waist formed from two portions of the first wire and two portions of the second wire. The first geometric form of the first wire and the first geometric form of the second wire form a first plate in a first plane. The second geometric form of the first wire and the second geometric form of the second wire form a second plate in a second plane that is parallel to and remote from the first plane. The first plane is disposed within a first spatial quartile and a second spatial quartile that is adjacent to the first spatial quartile. The second plane is disposed within a third spatial quartile and a fourth spatial quartile. The third spatial quartile is parallel to the first spatial quartile. The fourth spatial quartile is parallel to the second spatial quartile and adjacent to the third spatial quartile. The first geometric form of the first wire is disposed in the first spatial quartile. The second geometric form of the first wire is disposed in the fourth spatial quartile. The first geometric form of the second wire is disposed in the second spatial quartile. The second geometric form of the second wire is disposed in the third spatial quartile.

In accordance with an exemplary embodiment, a device for occluding an aperture in a tissue or vessel is provided. The device comprises a first flexible wire and a second flexible wire. Each of the first and second wires is comprised of a shape memory material. Each of the first and second wires is shaped into a first, a second, and a third geometric form. The first geometric form of the first wire and the first geometric form of the second wire form a first plate in a first plane. The second geometric form of the first wire and the second geometric form of the second wire form a second plate in a second plane that is parallel to and remote from the first plane. The third geometric form of the first wire and the third geometric form of the second wire form a third plate in a third plane that is parallel to and remote from both the first and second planes. The first and second plates are separated by a first waist formed from two portions of the first wire and two portions of the second wire. The second and third plates are separated by a second waist formed from an additional two portions of the first wire and an additional two portions of the second wire.

In accordance with another exemplary embodiment, a device for occluding an aperture in a tissue or vessel is provided. The device comprises a first flexible wire and a second flexible wire. Each of the first and second wires is comprised of a shape memory material. Each of the first and second wires is shaped into first and second geometric forms. The first geometric form of the first wire and the first geometric form of the second wire form a first plate in a first plane, and the second geometric form of the first wire and the second geometric form of the second wire form a second plate in a second plane that is parallel to and remote from the first plane. The first and second plates are separated by a waist formed from two portions of the first wire and two portions of the second wire, the waist comprising a flexible connection between the first and second plates.

In accordance with another exemplary embodiment, a device for occluding an aperture in a tissue or vessel is provided. The device comprises a first flexible wire and a second flexible wire. Each of the first and second wires is comprised of a shape memory material. Each of the first and second wires is shaped into first and second geometric forms. The first geometric form of the first wire and the first geometric form of the second wire form a first plate in a first plane, and the second geometric form of the first wire and the second geometric form of the second wire form a second plate in a second plane that is parallel to and remote from the first plane. The first and second plates are separated by a waist formed from two portions of the first wire and two portions of the second wire, the waist having a stored length.

In accordance with another exemplary embodiment, a device for occluding an aperture in a tissue or vessel is provided. The device comprises a first flexible wire and a second flexible wire. Each of the first and second wires is comprised of a shape memory material. Each of the first and second wires is shaped into first and second geometric forms. The first geometric form of the first wire and the first geometric form of the second wire form a first plate in a first plane, and the second geometric form of the first wire and the second geometric form of the second wire form a second plate in a second plane that is parallel to and remote from the first plane. The first and second plates are separated by a waist formed from two portions of the first wire and two portions of the second wire. The two portions of the first wire and the two portions of the second wire form a spring between the first and second plates.

In accordance with another exemplary embodiment, a device for occluding an aperture in a tissue or vessel is provided. The device comprises a first flexible wire and a second flexible wire. Each of the first and second wires is comprised of a shape memory material. Each of the first and second wires is shaped into first and second geometric forms. The first geometric form of the first wire and the first geometric form of the second wire form a first plate in a first plane, and the second geometric form of the first wire and the second geometric form of the second wire form a second plate in a second plane that is parallel to and remote from the first plane. The first and second plates are separated by a waist formed from two portions of the first wire and two portions of the second wire. The first plate, the second plate, or both, includes a flexible connection formed therein.

In accordance with another exemplary embodiment, a device for occluding an aperture in a tissue or vessel is provided. The device comprises a first flexible wire and a second flexible wire. Each of the first and second wires is comprised of a shape memory material. Each of the first and second wires is shaped into first and second geometric forms. The first geometric form of the first wire and the first geometric form of the second wire form a first plate in a first plane, and the second geometric form of the first wire and the second geometric form of the second wire form a second plate in a second plane that is parallel to and remote from the first plane. The first and second plates are separated by a waist formed from two portions of the first wire and two portions of the second wire. The first plate, the second plate, or both, has a stored length.

In accordance with another exemplary embodiment, a device for occluding an aperture in a tissue or vessel is provided. The device comprises a first flexible wire and a second flexible wire. Each of the first and second wires is comprised of a shape memory material. Each of the first and second wires is shaped into first and second geometric forms. The first geometric form of the first wire and the first geometric form of the second wire form a first plate in a first plane, and the second geometric form of the first wire and the second geometric form of the second wire form a second plate in a second plane that is parallel to and remote from the first plane. The first and second plates are separated by a waist formed from two portions of the first wire and two portions of the second wire. The first plate, the second plate, or both, includes a spring formed therein.

In accordance with another exemplary embodiment, a device for occluding an aperture in a tissue or vessel is provided. The device comprises a first flexible wire and a second flexible wire. Each of the first and second wires is comprised of a shape memory material. Each of the first and second wires is shaped into first and second geometric forms. The first geometric form of the first wire and the first geometric form of the second wire form a first plate in a first plane, and the second geometric form of the first wire and the second geometric form of the second wire form a second plate in a second plane that is parallel to and remote from the first plane. The first and second plates are separated by a waist comprising a first waist component from the first wire and a second waist component from the second wire. In some embodiments the first and second waist components are not substantially centered about a center axis of the device.

In accordance with another exemplary embodiment, a device for occluding an aperture in a tissue or vessel is provided. The device comprises a first flexible wire and a second flexible wire. Each of the first and second wires is comprised of a shape memory material. Each of the first and second wires is shaped into first and second geometric forms. The first geometric form of the first wire and the first geometric form of the second wire form a first plate in a first plane, and the second geometric form of the first wire and the second geometric form of the second wire form a second plate in a second plane that is parallel to and remote from the first plane. The first and second plates are separated by a waist formed by the first wire and the second wire. The first wire crosses a center region of the device at a first point and a second point. The second wire crosses the center region at a third point and a fourth point. The first, second, third, and fourth points form a substantially square shape therebetween.

In accordance with yet other exemplary embodiments, methods for occluding an aperture in a tissue or vessel are provided. The methods comprise the steps of providing an occluder device of a type corresponding to one of the various occluder device embodiments described herein. The occluder device further comprises a sealed covering over at least one of the first and second plates, wherein the covering provides a seal for the aperture. Each of the first and second wires has a first and second end. Each of the first and second ends of the first and second wires is connected to a hub. The hub further comprises a delivery attachment mechanism for attachment to a removable deployment cable. The methods further comprise attaching the occluder device to the removable deployment cable, placing the occluder device within a flexible delivery catheter having an open channel, feeding the catheter into a blood vessel system and advancing the catheter via the blood vessel system to the aperture. The catheter is advanced through the aperture, and is withdrawn from the occluder device such that the first plate of the occluder device expands on a first side of the aperture. The catheter is further withdrawn from the occluder device such that the second plate of the occluder device expands on a second side of the aperture, such that the waist of the occluder device expands by memory retention within the aperture to self-center the occluder device. The catheter is further withdrawn from the blood vessel system, and the deployment cable is removed from the hub.

Other advantages, benefits and novel features of the embodiments of the present invention will become apparent from the following detailed description and accompanying drawings. All references, publications and patents, including the figures and drawings included therewith, are incorporated by reference in their entirety.

BRIEF DESCRIPTION OF THE DRAWINGS

The present disclosure will hereinafter be described in conjunction with the following drawing figures, wherein like numerals denote like elements.

DETAILED DESCRIPTION

The following detailed description is merely exemplary in nature and is not intended to limit the disclosure or the application and uses of the disclosure. Furthermore, there is no intention to be bound by any theory presented in the preceding background or the following detailed description.

The present disclosure provides a device for occluding an aperture within body tissue or vessel. One skilled in the art will recognize that the device and methods of the present disclosure may be used to treat other anatomical conditions in addition to those specifically discussed herein. As such, the disclosure should not be considered limited in applicability to any particular anatomical condition.

Figure 1:
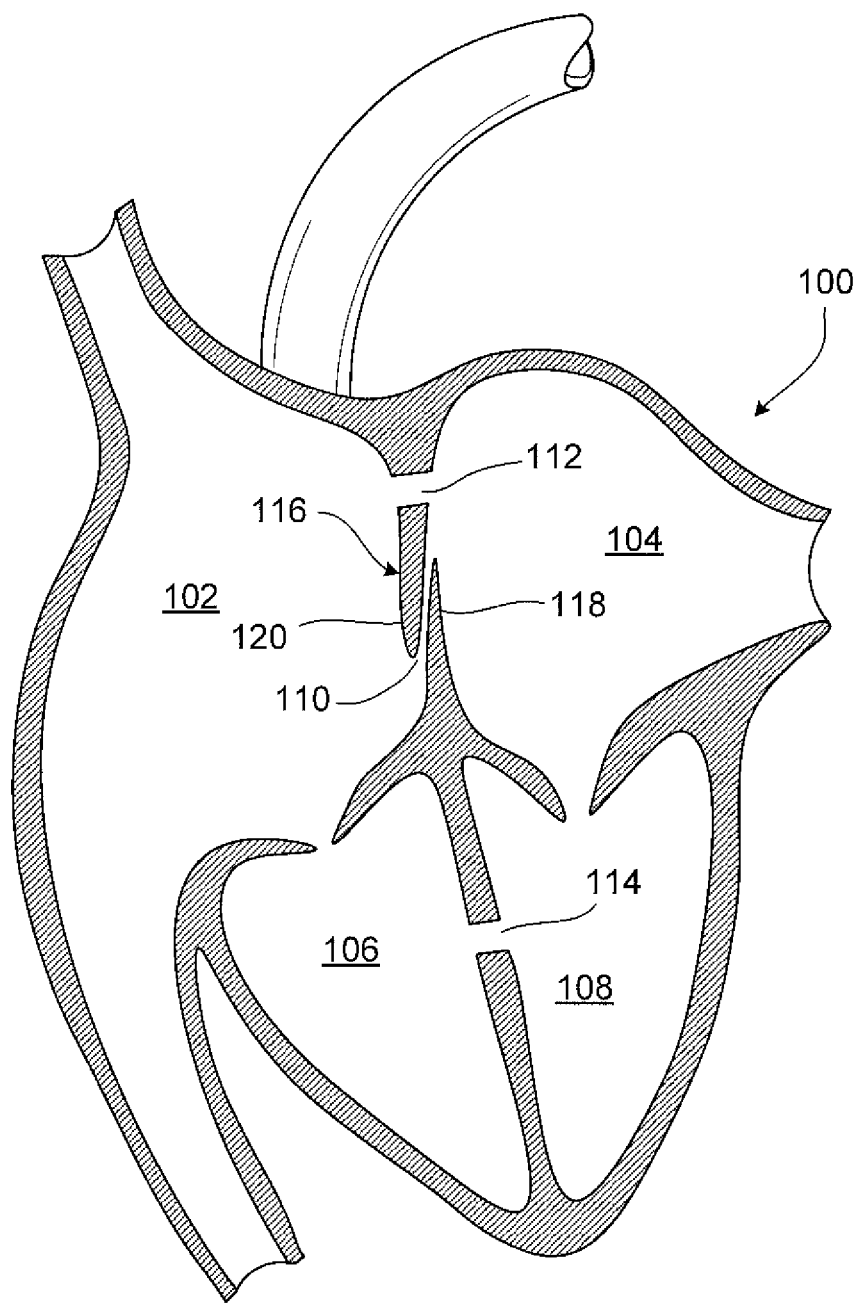
FIG. 1 is a schematic representation of a human heart including various septal defects, in accordance with an exemplary embodiment.

As described herein, FIG. 1 illustrates a human heart 100, having a right atrium 102, a left atrium 104, a right ventricle 106, and a left ventricle 108. Shown are various anatomical anomalies 110, 112, and 114. The atrial septum 116 includes septum primum 118 and septum secundum 120. The anatomy of the septum 116 varies widely within the population. In some people, the septum primum 118 extends to and overlaps with the septum secundum 120. The septum primum 118 may be quite thin. When a PFO is present, blood could travel through the passage 110 between septum primum 118 and septum secundum 120 (referred to as "the PFO tunnel"). Additionally or alternatively, the presence of an ASD could permit blood to travel through an aperture in the septal tissue, such as that schematically illustrated by aperture 112. A VSD is similar to an ASD, except that an aperture 114 exists in the septum between the left and right ventricle of the heart.

PDA results from defects in the ductus arteriosus. The human blood circulation comprises a systemic circuit and a pulmonary circuit. In the embryonic phase of human development, the two circuits are joined to one another by the ductus arteriosus. The ductus connects the aorta (circulation to the body) to the pulmonary artery (pulmonary circuit). In normal development of an infant, this ductus closes after birth. If development is defective, it can happen that the ductus does not close, and as a result the two blood circuits are still joined even after birth.

As used herein, "distal" refers to the direction away from a catheter insertion location and "proximal" refers to the direction nearer the insertion location. As used herein, "memory" or "shape memory" refers to a property of materials to resume and maintain an intended shape despite being distorted for periods of time, such as during storage or during the process of delivery in vivo.

As used herein, "aperture" refers to a gap, hole or opening in a patient's body. Apertures may be in a tissue (including, for example, in an organ), or a vessel. By way of example, apertures in heart tissue include, but are not limited to, PFO, ASD, VSD, and PDA, among others. Apertures in vessels include apertures in the walls of vessels (e.g., focal aortic defects, pseudoaneurysms, penetrating ulcers or communicative defects between the true and false lumen in aortic dissections) as well as the arteries or veins themselves wherein the aperture refers to the lumen of the vessel.

Referring now to FIGS. 2-15, an occluder device 200 of the present disclosure is provided. While for the sake of brevity, the term "occluder device 200" is used generically throughout, it is to be understood that in embodiments or descriptions where no covering is depicted or described, the embodiment is referring to an "occluder frame". Similarly, it is to be understood that in embodiments where a covering is depicted or described, the embodiment is referring to an "occluder device".

The occluder device 200 is configured to occlude an aperture, including, for example, a defect of a heart, such as one or more of the anomalies 110, 112, 114 of the heart 100 depicted in FIG. 1. One skilled in the art would also recognize the device's application for use as a vascular occluder or plug as well as an atrial appendage occluder.

Figure 2:
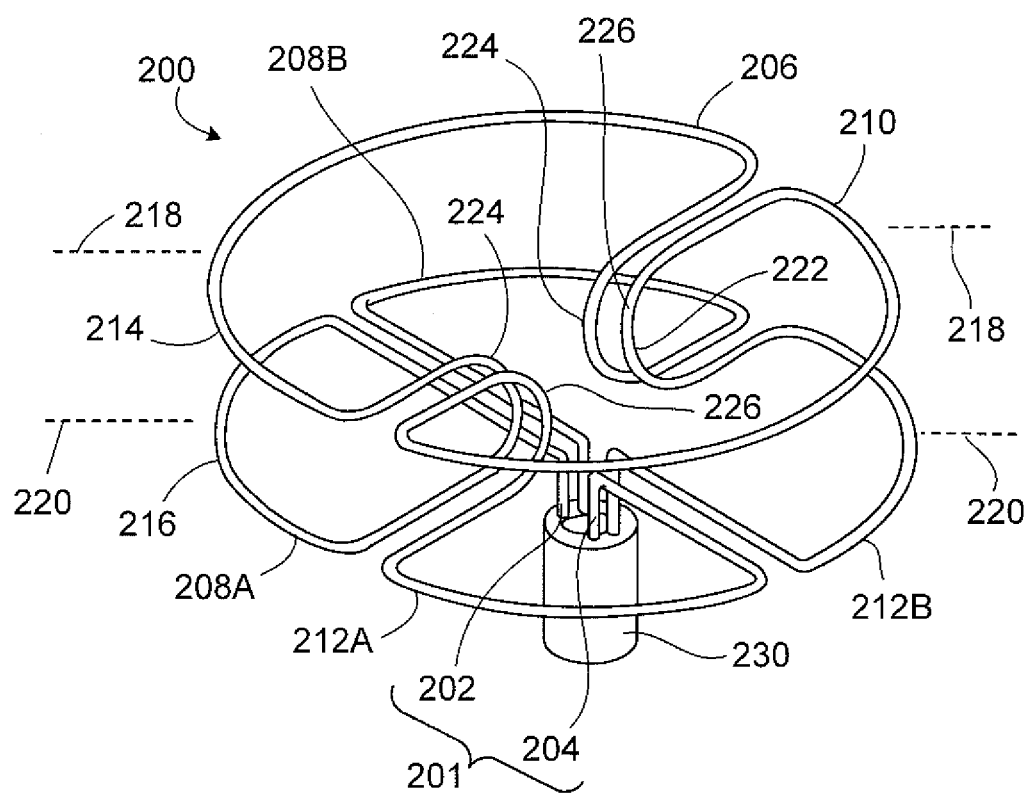
FIG. 2 is a perspective view of an occluder device, in accordance with an exemplary embodiment.
Figure 3:
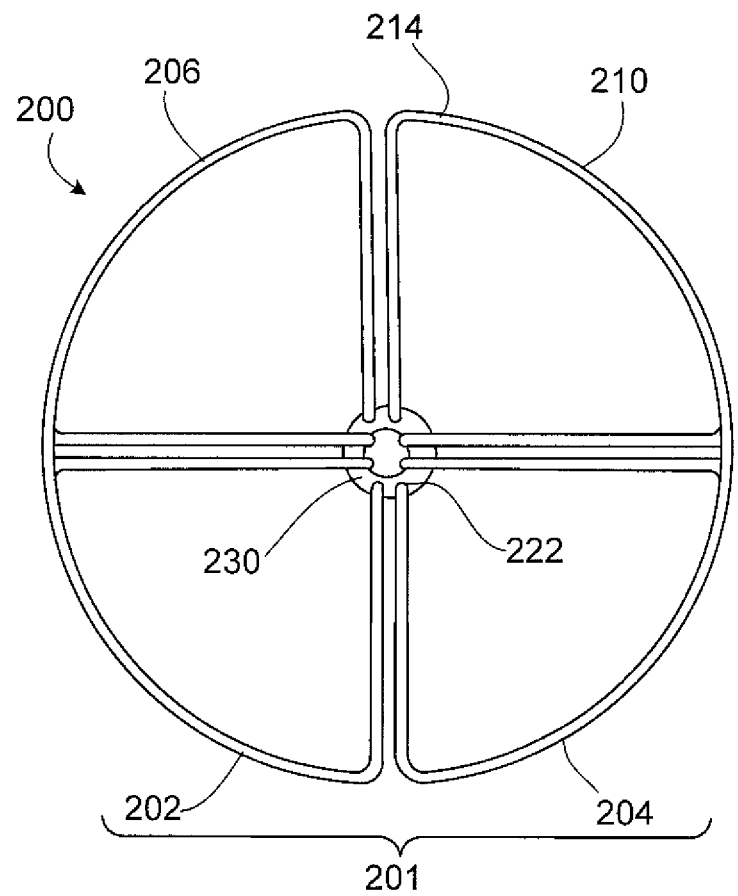
FIG. 3 is a top plan view of the occluder device of FIG. 2, in accordance with an exemplary embodiment.
Figure 4:
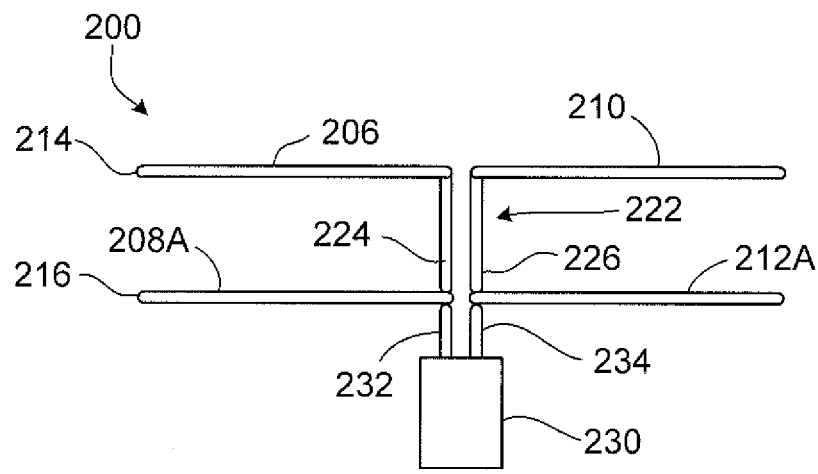
FIG. 4 is a side plan view of the occluder device of FIG. 2, in accordance with an exemplary embodiment.
Figure 5:
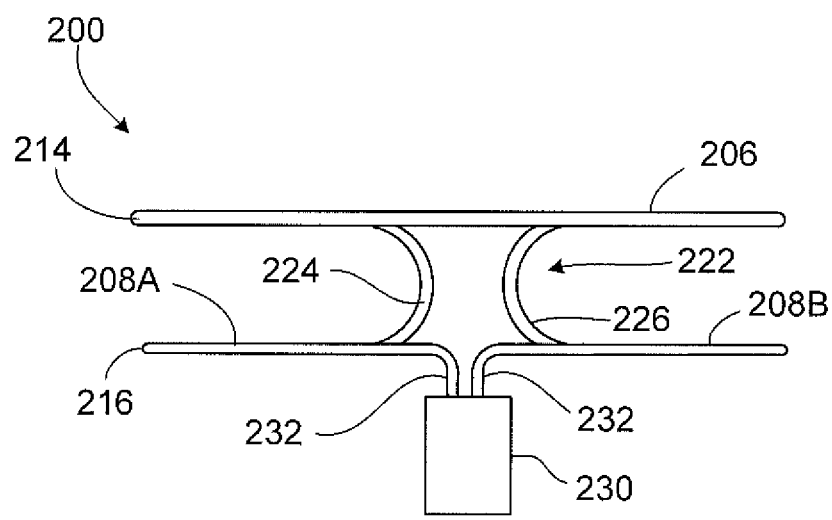
FIG. 5 is a side plan view of the occluder device of FIG. 2, in accordance with an exemplary embodiment.

As depicted in FIG. 2 the occluder device 200 comprises two separate uniquely shaped memory wires 201. While in some embodiments one member of the pair of shaped memory wires has a shape different than the shape of the other member of the pair, in some embodiments each member of the pair of shaped memory wire has a shape identical to the shape of the other member of the pair. The memory wires 201 can be formed of biocompatible metals or polymers, such as bioresorbable polymers, shape memory polymers, shape memory metal alloys, biocompatible metals, bioresorbable metals, or combinations thereof. Specific examples include but are not limited to iron, magnesium, stainless steel, nitinol, or combinations of these and/or similar materials. A preferred metal for the present disclosure is a nitinol alloy. Nitinol (an acronym for Nickel Titanium Naval Ordinance Laboratory) is a family of intermetallic materials, which contain a nearly equal mixture of nickel (55 wt. %) and titanium. Other elements can be added to adjust or "tune" the material properties. Nitinol exhibits unique behavior, specifically, a well-defined "shape memory" and super elasticity. In general, any biocompatible material with a memory capability can be used with the present disclosure. The thermal shape memory and/or superelastic properties of shape memory polymers and alloys permit the occluder device 200 to resume and maintain its intended shape in vivo despite being distorted during the delivery process. In certain embodiments, the memory may also assist in pressing an aperture, such as a PFO tunnel, closed. The diameter or thickness of the wire depends on the size and type of the device, i.e., the larger the device, the larger the diameter of the wire. In general, wire having a diameter between about 0.2 mm and 0.8 mm can be used.

In some embodiments the occluders include three or more, four or more, five or more, or six or more separate uniquely shaped memory wires. While in some such embodiments, one or more of the shaped memory wires has a shape different than the shape of the other shaped memory wires, in some embodiments two or more of the memory wires have an identical shape, in other embodiments each of the shaped memory wires has an identical shape.

In the embodiments of FIGS. 2-5, the memory wires comprise a first wire 202 and a second wire 204. In certain embodiments, the memory wires 201 may further comprise one or more additional wires. In the embodiment of FIGS. 2-5, each wire 202, 204 forms a shape which mirrors that of the other respective wire 204, 202. In other embodiments, the respective shapes of the different wires 201 may be otherwise related to one another, for example via a diagonal or double-mirrored relationship.

The first wire 202 forms one or more first geometric forms 206 and one or more second geometric forms 208. "Geometric forms" as used herein comprises symmetric as well as asymmetric forms. Relative to a delivery attachment mechanism or hub 230, discussed below in greater detail, the first geometric form 206 of the first wire 202 preferably comprises a distal geometric form, and the second geometric forms 208 of the first wire preferably each comprise proximal geometric forms. In the embodiments of FIGS. 2-5, there is a single first, or distal, geometric form 206 of the first wire 202. Also in the embodiment of FIGS. 2-5, there are two second, or proximal, geometric forms 208 of the first wire 202 (namely, 208(A) and 208(B)). However, the number and configuration of the first and/or second geometric forms 206, 208 of the first wire 202 may vary.

Similarly the second wire 204 forms a first geometric form 210 and a second geometric form 212. Relative to the hub 230, the first geometric form 210 of the second wire 204 preferably comprises a distal geometric form, and the second geometric form 212 of the second wire preferably comprises a proximal geometric form. In the embodiment of FIGS. 2-5, there is a single first, or distal, geometric form 210 of the second wire 204. Also in the embodiment of FIGS. 2-5, there are two second, or proximal, geometric forms 212 of the second wire 204 (namely, 212(A) and 212(B)). However, the number and configuration of the first and/or second geometric focus 210, 212 of the second wire 204 may vary.

The first geometric forms 206 of the first wire 202 and the first geometric forms 210 of the second wire 204 form a first plate, such as a disc, or another otherwise relatively flat surface (hereinafter referred to as a "plate") 214 in a first plane 218. The second geometric forms 208 of the first wire 202 and the second geometric forms 212 of the second wire 204 form a second plate 216 in a second plane 220 that is parallel to and remote from the first plane 218. In the embodiment of FIGS. 2-5, the first and second plates 214, 216 each comprise one or more semi-circular discs. However, this may vary in other embodiments, as the first and second plates 214, 216 may comprise any one or more of a number of other different types of geometric forms.

Specifically, in the embodiment of FIGS. 2-5, each wire 202, 204 forms a respective distal semi-circle or half disc 206, 210 in addition to two proximal quarter-circles or quarter-discs 208(A), 208(B) or 212(A), 212(B). The two proximal quarter-circles of each wire together form proximal semi-circles or half-discs 208(A), 208(B) or 212(A), 212(B). The two distal semi-circles of each respective wire 202, 204 together comprise a distal plate 214 (depicted in FIGS. 2-5 as a distal disc) of the occluder device 200. The four proximal quarter-circles 208(A), 208(B), 212(A), 212 (B), which form a "four-leaf clover" configuration in the embodiment of FIGS. 2-5, comprise a proximal plate 216 (depicted in FIGS. 2-5 as a proximal disc) of the occluder device 200.

In the embodiment of FIGS. 2-5, the proximal semi-circle 208(A), 208(B) or 212(A), 212(B) of each wire 201 is connected to the distal semi-circle 206 or 210 by a waist 222 formed by waist components 224, 226. As shown in FIG. 2, there are two waist components 224 of the first wire 202 and two waist components 226 of the second wire 204. The four waist components (two from each wire) 224, 226 together comprise restricted area or waist 222 of the occluder device 200. The distance between the waist components, both within the same wire and from wire to wire, determines the size of the waist 222. The size of the waist 222 is dependent on the particular application and the size of the occluder device 200. The resiliency and memory of the waist components 224, 226 and capacity to expand radially serves as a self-centering mechanism of the occluder device 200 in heart apertures. The first and second wires 202, 204 are attached, joined, or otherwise coupled to the delivery attachment mechanism or hub 230. The ends 232, 234 of wires 202, 204 are welded, glued, or otherwise affixed to the hub 230.

Figure 6:
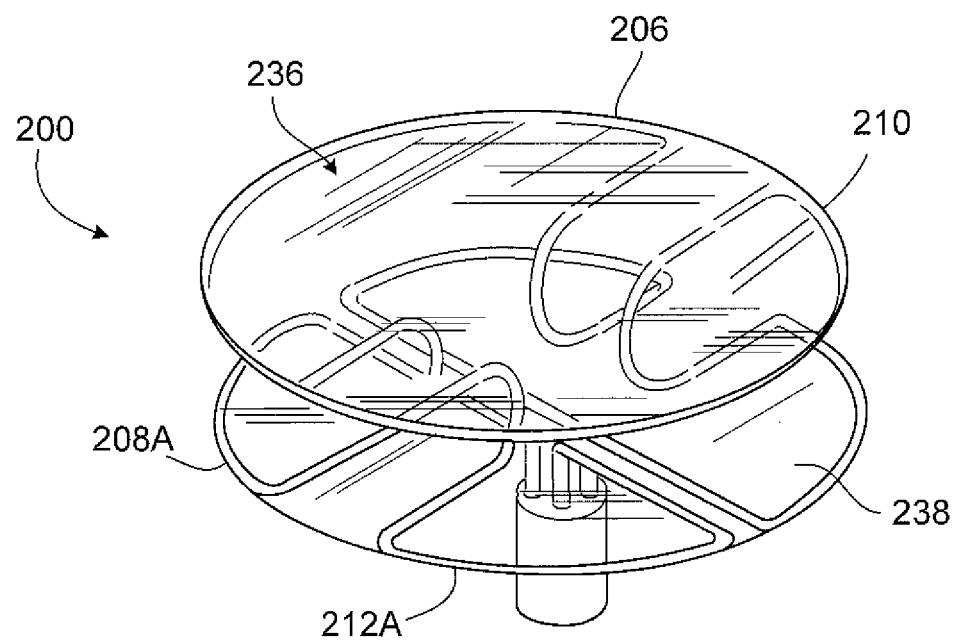
FIG. 6 is a perspective view of the occluder device of FIG. 2, and illustrating a cover for the occluder device, in accordance with an exemplary embodiment.
Figure 7:
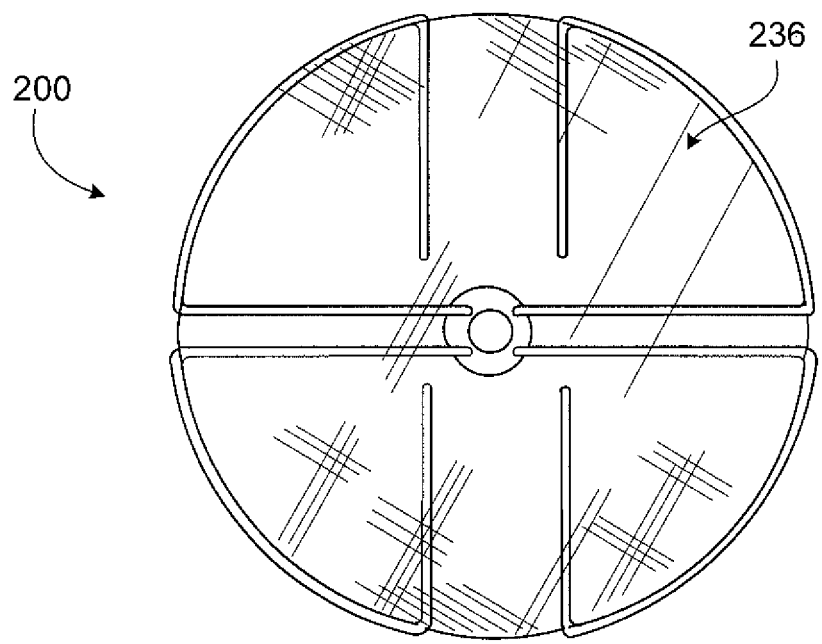
FIG. 7 is a top plan view of the occluder device of FIG. 2, depicted along with the cover of FIG. 6, in accordance with an exemplary embodiment.

According to certain embodiments contemplated herein, the distal plate 214 and/or proximal plate 216 may include membranous coverings 236 and 238 illustrated in FIGS. 6 and 7. The membranous coverings 236 and 238 ensure more complete coverage of an aperture and promote encapsulation and endothelialization of tissue, thereby further encouraging anatomical closure of the tissue and improving closure rate. The coverings 236 and 238 also help stabilize the occluder device 200.

In FIGS. 6 and 7, the plates are depicted as including respective coverings. For example, coverings 236 and 238 are depicted in FIG. 6 and covering 236 is depicted in FIG. 7. Similarly, the third plate 217 described further below in connection with FIG. 12 may also include a similar membranous covering. However, in certain embodiments one or more of the plates may include a covering, while certain other of the plates may not include a covering. In some embodiments, one or more of the plates are at least partially covered with a membranous covering. In addition, in certain embodiments, the waist (not shown in FIG. 6 or FIG. 7) may also include a membranous covering, while in other embodiments the waist may not include a membranous covering. In some embodiments the waist is partially covered with a membranous covering.

The membranous coverings 236 and 238 may be formed of any flexible, biocompatible material capable of promoting tissue growth and/or acting as a sealant. Examples of suitable membranous coverings include, but are not limited to DACRON®, polyester fabrics, Teflon-based materials, ePTFE, polyurethanes, metallic materials, polyvinyl alcohol (PVA), extracellular matrix (ECM) or other bioengineered materials, synthetic bioabsorbable polymeric materials, other natural materials (e.g. collagen), or combinations of the foregoing materials. For example, the membranous coverings 236 and 238 may be formed of a thin, metallic film or foil, e.g. a nitinol film or foil, as described in U.S. Pat. No. 7,335,426 (the entirety of which is incorporated herein by reference). One preferred material is expanded polytetrafluoroethylene (ePTFE) as it combines several important features such as thickness and the ability to stretch. Loops may also be stitched to the membranous coverings 236 and 238 to securely fasten the coverings to occluder device 200. The coverings may additionally or alternatively be glued, welded or otherwise attached to the occluder device 200 via the wires (not shown in FIG. 6 or FIG. 7).

As noted above, the microporous structure of the membranous coverings can be tailored to promote tissue ingrowth and/or endothelialization. For example, the coverings can be modified by various chemical or physical processes to enhance certain mechanical or physical properties. A hydrophilic coating can be applied to the covering to promote its wetability and/or echo translucency. Additionally, physiochemical modifications can be employed whereby the covering includes chemical moieties that promote endothelial cell attachment, migration, and/or proliferation or resist thrombosis. A surface modified with covalently attached heparin is one example of a covering modification.

While in some embodiments the coverings prevent blood flow through the aperture, e.g. acute occlusion, in other embodiments the microporosity of the coverings permits some blood flow through the aperture, e.g. partial occlusion. In some such embodiments, this blood flow is reduced over time by tissue ingrowth and/or endothelialization of the covering.

In some embodiments, the plates 214, 216 are of equal size and are centered around the hub 230. In other embodiments, the plates 214, 216 may be of unequal sizes. In yet other embodiments, the plates 214, 216 may be of equal size yet offset from each other via a shift in opposite directions from the hub 230.

The diameters of the distal plate 214 and proximal plate 216 are generally 5-8 mm larger than the diameter of the connecting waist 222. For example, if the diameter of the connecting waist 222 is 4 mm, the diameters of the plates 214, 216 are generally about 9 mm each. Because of the flexibility in the waist 222, a 12 mm waist device will be able to be placed in a 6 mm to 12 mm defect. For larger waists 222 or larger devices, the diameter of the plate size will increase proportionately.

It is within the scope of the present disclosure to envision occluder devices available in multiple different sizes. In some embodiments, devices include waist sizes having the following diameters: 6 mm, 12 mm, 18 mm, 24 min, 30 mm, 36 mm, and 42 mm.

In general, the occluder device 200 may be inserted into an aperture to prevent the flow of blood therethrough. As a non-limiting example, the occluder device 200 may extend through a PFO 110 or an ASD 112 such that the distal plate 214 is located in the left atrium 104 and the proximal plate 216 is located in the right atrium 102 (as shown in the heart 100 in FIG. 1). As mentioned above, one skilled in the art would also recognize the application of the occluder device 200 for use as a vascular occluder or plug as well as an atrial appendage occluder. The closure of apertures in these and other tissues, as well as other types of apertures, will become apparent as described below.

Figure 8:
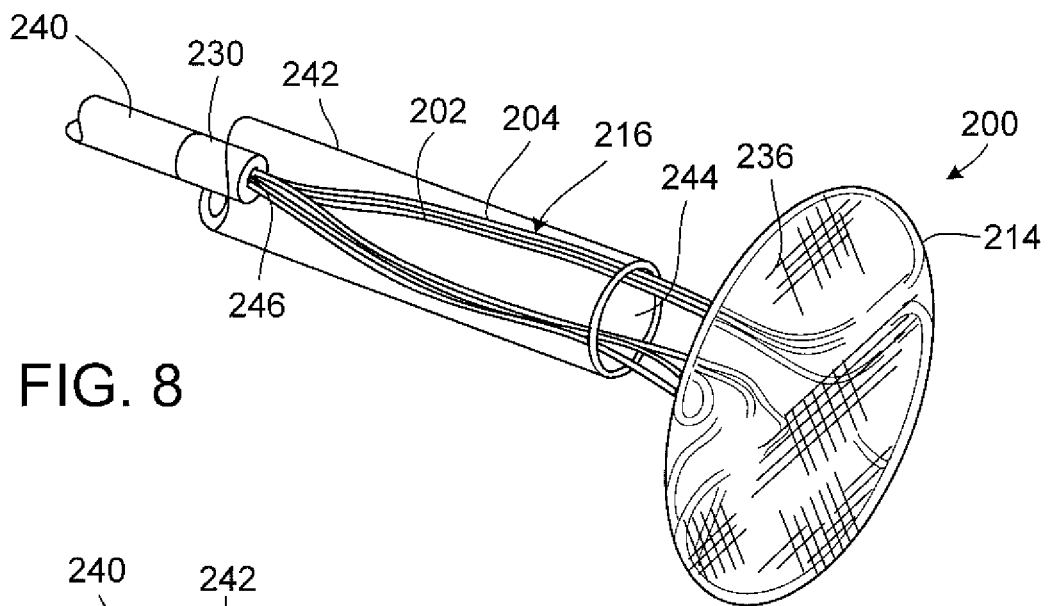
FIG. 8 is a perspective view of the occluder device of FIG. 2, depicted as first emerging from a catheter, in accordance with an exemplary embodiment.
Figure 9:
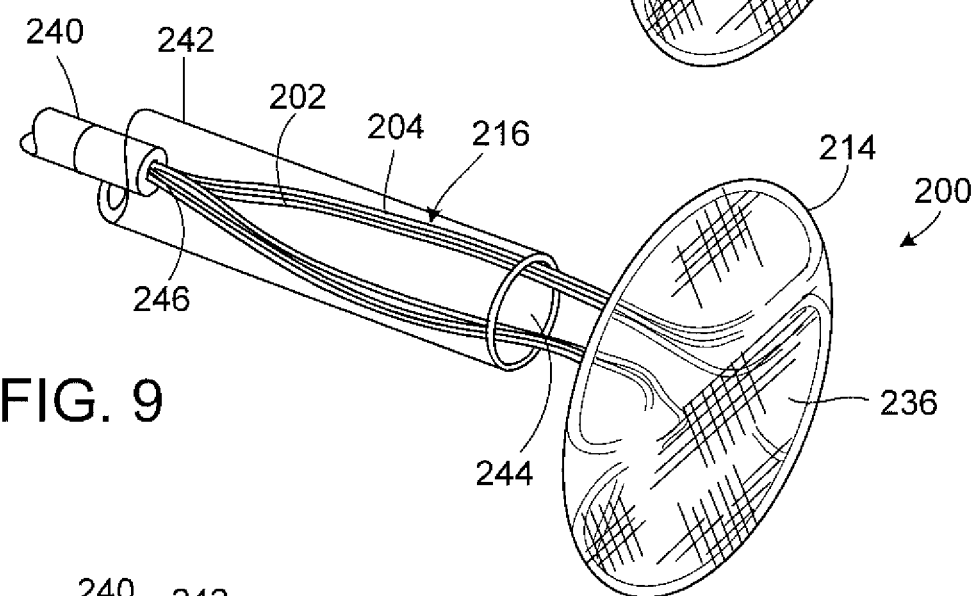
FIG. 9 is a perspective view of the occluder device of FIG. 2, depicted as half-way merged from the catheter, in accordance with an exemplary embodiment.
Figure 10:
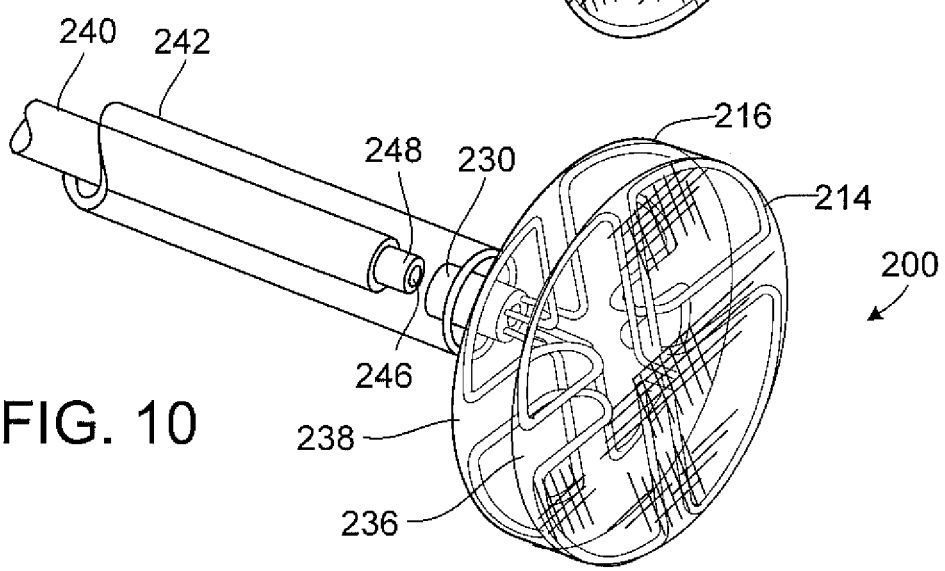
FIG. 10 is a perspective view of the occluder device of FIG. 2, depicted as fully emerged from the catheter and separated from a deployment cable, in accordance with an exemplary embodiment.

Referring now to FIGS. 8-10, the occluder device 200 is attached to a deployment cable 240 which is removably attached to the occluder device 200 at the hub 230. As illustrated in FIG. 10, one method of releasably attaching the deployment cable 240 to the hub 230 is by threaded engagement utilizing a screw end 248 which engages unseen female threads within the hub 230. Other known means of attachment can be used to releasably connect the deployment cable 240 to the hub 230.

In some embodiments the occluder device 200 includes hub 230 at both the proximal and distal ends of the device to allow the user to conveniently select the orientation of the device. As described below, the hub 230 also permits the user to reposition the device if so desired.

When the deployment cable 240 is engaged with the hub 230, as illustrated in FIGS. 8 and 9, the occluder device 200 is initially housed within a flexible delivery catheter 242 having an open channel 244. Reference is made to FIG. 8 which illustrates the occluder device 200 in which the distal plate 214 is expanded, due to the memory expansion of the wires 202 and 204, and housed within the open channel 244 of the delivery catheter 242. During the initial stages of placement of the occluder device 200, both the distal plate 214 and the proximal plate 216 as well as the coverings 236 and 238 are housed within the open channel 244 of the delivery catheter 242. In this manner, the catheter 242 is fed into a blood vessel through an already placed sheath and advanced via the blood vessel system to an aperture, including, for example, apertures in tissue (e.g. apertures in the heart including the PFO, the ASD, the VSD, the PDA, or an atrial appendage). As described above, occluders may also be used to close or block the lumen of a vessel or to close or block an aperture in the wall of a vessel.

Once the delivery catheter 242 traverses the aperture to be occluded, e.g., a hole in the heart, the occluder device 200 will be partially advanced from the catheter 242 as illustrated in FIG. 8. As the occluder device 200 leaves the catheter 242, the distal plate 214, which includes the covering 236, begins to expand on the distal side of the aperture. Due to the memory capabilities of the wires 202 and 204, the occluder device 200 begins to return to its normal shape such that the distal plate 214 expands on the distal side of the aperture. Once the distal plate 214 is completely out of the catheter opening 244, as shown in FIG. 9, the distal plate 214 and the attached covering 236 become fully expanded. The catheter 242 is further withdrawn to expose the waist 222, which then begins to emerge and expand due to the memory shape of the wires 202 and 204. Advantageously, the waist 222 is designed to expand such that each of the wires forming the waist 222 is urged against the aperture causing a custom fit device of the occluder device 200 within the aperture. As the catheter 242 is further withdrawn, the proximal plate 216 and the covering 238 begin their process of expansion on the proximal side of the aperture. When the proximal plate 216 is fully delivered from the catheter 242, it will expand and effectively form a seal over the aperture. The distal plate 214 and proximal plate 216 are secured in place by the action of the wires in the waist 222 urging against the aperture. At this stage, as shown in FIG. 10, the deployment cable 240 is removed from the hub 230 and the catheter 242 and the deployment cable 240 are removed from the body. The occluder device 200 is left at the region of the aperture. Over several months, tissue and other membranous structures will bind to the occluder device 200 thereby permanently locking the occluder device 200 to the specific area of the aperture.

The two wires 202, 204 function to form round plates 214, 216 on each side of the aperture. The plates 214, 216 maintain the circular shape because of the memory capability of the wires 202, 204. In some embodiments the coverings 236, 238 help to stabilize the discs, and preferably act to completely occlude the defect.

In embodiments where self-centering is desired, the wires 202, 204 at the waist components 224, 226 will be separated enough at the waist 222 to make the occluder device 200 self-centering. Due to the conformity of this design, the occluder device 200 will self-center within commonly (e.g. round, oval) shaped septal defects as the waist 222 can adjust to any type of opening.

If a larger-diameter waist 222 is required, the waist 222 has the capability to expand (if needed) to a larger size with the help of a balloon. In this manner, a center channel 246 extends through the deployment cable 240, the hub 230, and the screw end 248. A balloon (not shown) is urged through the center channel 246 after the occluder device has been removed from the catheter 242 and expanded but before the hub 230 has been detached from the deployment cable 240. The balloon is placed within the waist 222 and expanded. The waist 222 is dilatable, i.e., expandable, when gentle pressure of the balloon is applied. The dilation will expand the waist components 224, 226. Once the desired diameter is reached, the balloon is deflated and removed by withdrawal through the center channel 246. Once the occluder device 200 appears stable, the occluder device 200 is separated from the deployment cable 240 as discussed above. In the majority of cases, balloon dilation will not be required.

Figure 11:
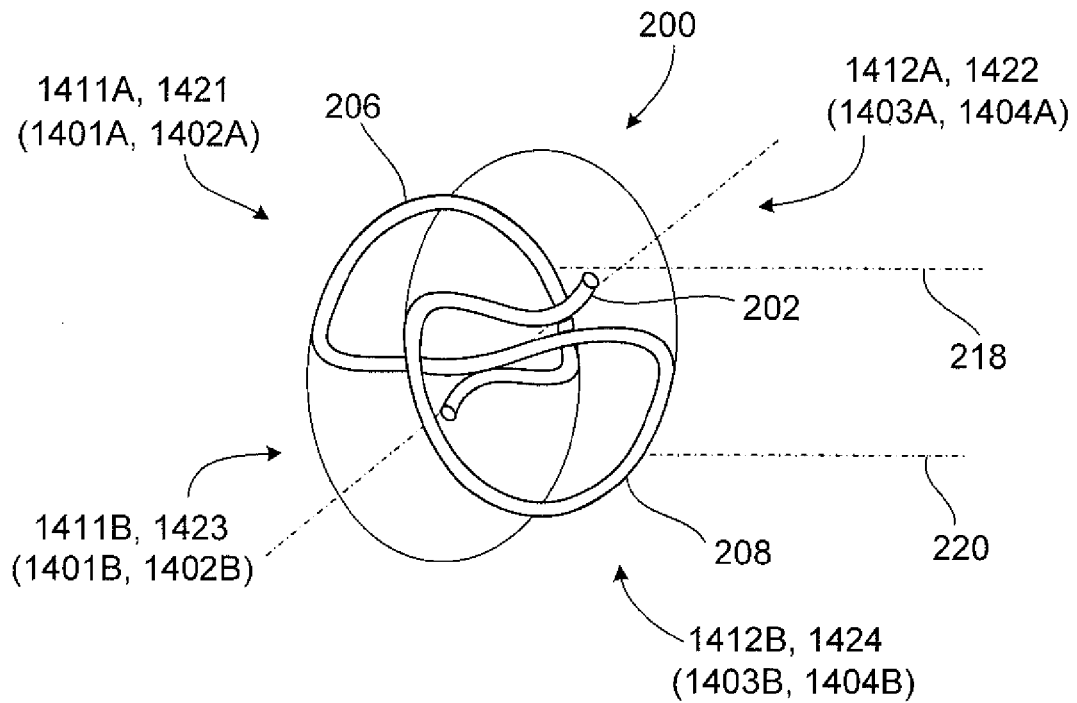
FIG. 11 is a perspective view of another exemplary alternative embodiment of an occluder device, depicted with reference to planar quadrants in FIG. 11A.
Figure 11A:
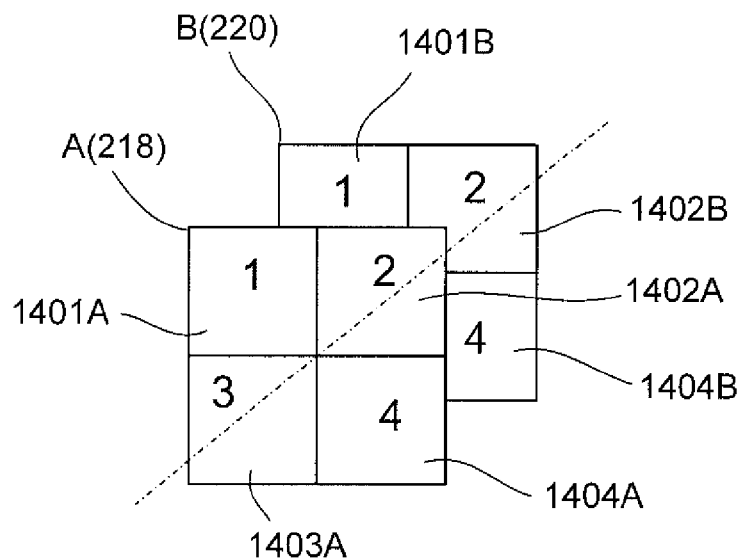

With reference to FIGS. 11-15, various exemplary embodiments are provided with respect to the occluder device and/or components thereof. FIGS. 11 and 11A depict an embodiment of an occluder device contemplated herein with first wire 202 and staggered geometric forms 206, 208 of the first wire 202. Not shown in FIG. 11 are the second wire and staggered geometric forms of the second wire. FIG. 11A depicts an exemplary classification of planar quadrants for the first and second planes 218, 220 of FIG. 2 for reference with respect to the embodiment of FIG. 11. One skilled in the art will recognize that less or more than four quadrants can be utilized.

With reference to FIGS. 11 and 11A, the first plane 218 of FIG. 2 has a first quadrant 1401(A), a second quadrant 1402(A) that is adjacent to the first quadrant 1401(A), a third quadrant 1403(A) that is below the first quadrant 1401(A), and a fourth quadrant 1404(A) that is below the second quadrant 1402(A) and adjacent to the third quadrant 1403 (A). The second plane 220 of FIG. 2 has a first quadrant 1401(B), a second quadrant 1402(B) that is adjacent to the first quadrant 1401(B), a third quadrant 1403(B) that is below the first quadrant 1401(B), and a fourth quadrant 1404(B) that is below the second quadrant 1402 (B) and adjacent to the third quadrant 1403(B). The first quadrant 1401(A) of the first plane 218 is closer to the first quadrant 1401(B) of the second plane 220 than to the second, third, or fourth quadrants 1402(B), 1403(B), 1404(B) of the second plane 220. The second quadrant 1402(A) of the first plane 218 is closer to the second quadrant 1402(B) of the second plane 220 than to the first, third, or fourth quadrants 1401(B), 1403(B), 1404(B) of the second plane 220. The third quadrant 1403(A) of the first plane 218 is closer to the third quadrant 1403(B) of the second plane 220 than to the first, second, or fourth quadrants 1401(B), 1402(B), 1404(B) of the second plane 220. The fourth quadrant 1404(A) of the first plane 218 is closer to the fourth quadrant 1404(B) of the second plane 220 than to the first, second, or third quadrants 1401(B), 1402(B), 1403(B) of the second plane 220.

In the depicted embodiment of FIG. 11, the first geometric form 206 of the first wire 202 extends through the first and second quadrants 1401(A), 1402(A) of the first plane 218, preferably in a hemispheric shape. The second geometric form 208 of the first wire 202 extends through the third and fourth quadrants 1403(B), 1404(B) of the second plane 220, also preferably in a hemispheric shape. The two hemispheric shapes are joined by a portion of the first wire 202 that extends in an angled manner from the first plane 218 to the second plane 220. Not shown in FIG. 11 are depictions of the first geometric form of the second wire extending through the third and fourth quadrants of the first plane, preferably in a hemispheric shape. Not shown in FIG. 11 is the second geometric form of the second wire 204 extending through the first and second quadrants of the second plane, also preferably in a hemispheric shape. The two hemispheric shapes are joined by a portion of the second wire that extends in an angled manner from the first plane to the second plane. Although the first wire 202 and second wire preferably form hemispheric shapes in planes 218, 220, the invention is not so limited, and various shapes suitable for in an occlusive device may be used.

The first plane 218 may also be considered to include a first half-plane 1411(A) and a second half-plane 1412(A). For example, the first half-plane 1411(A) may comprise the first and second quadrants 1401(A), 1402(A) of the first plane 218. Similarly, the second half-plane 1412(A) may comprise the third and fourth quadrants 1403(A), 1404(A) of the first plane 218.

Likewise, the second plane 220 may also be considered to include a first half-plane 1411(B) and a second half-plane 1412(B). For example, the first half-plane 1411(B) may comprise the first and second quadrants 1401(B), 1402(B) of the second plane 220. Similarly, the second half-plane 1412(B) may comprise the third and fourth quadrants 1403 (B), 1404(B) of the second plane 220.

Accordingly, also in the depicted embodiment, the first geometric form 206 of the first wire 202 extends through and is disposed within the first half-plane 1411(A) of the first plane 218. The second geometric form 208 of the first wire 202 extends through and is disposed within the second half-plane 1412(B) of the second plane 220. Not shown in FIG. 11 are depictions of the first geometric form of the second wire extending through and disposed within the second half-plane of the first plane. Also not shown in FIG. 11 is a depiction of the second geometric form of the second wire extending through and disposed within the first half-plane of the second plane.

The first and second planes 218, 220 may also collectively be considered to include four spatial quartiles 1421, 1422, 1423, and 1424. For example, the first spatial quartile 1421 may comprise the first half-plane 1411(A) of the first plane 218, the second spatial quartile 1422 may comprise the second half-plane 1412(A) of the first plane 218, the third spatial quartile 1403 may comprise the first half-plane 1411(B) of the second plane 220, and the fourth spatial quartile 1424 may comprise the second half-plane 1412(B) of the second plane 220.

Accordingly, also in the depicted embodiment, the first geometric form 206 of the first wire 202 extends through and is disposed within the first spatial quartile 1421, the second geometric form 208 of the first wire 202 extends through and is disposed within the fourth spatial quartile 1424. Not shown is the first geometric form of the second wire extending through and disposed within the second spatial quartile, and the second geometric form of the second wire extending through and disposed within the third spatial quartile.

Figure 12:
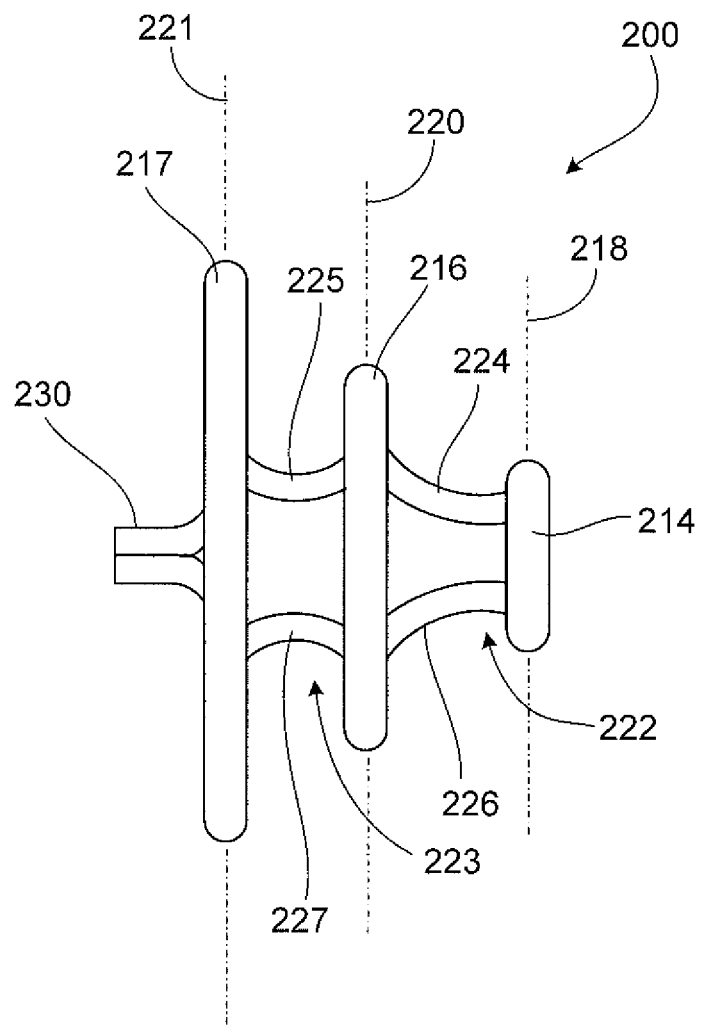
FIG. 12 is a side view of another exemplary alternative embodiment of an occluder device.

FIG. 12 depicts an embodiment of an occluder device contemplated herein with an increased number of plates and waists as compared with the embodiment of FIG. 2. Additional plates and waists may be beneficial, for example, in providing additional support and/or stability, and/or reaching apertures that are deeper within the heart or vessels, closing multiple apertures, and/or closing apertures that are surrounded by non-uniform tissue. In some implementations, the occluder device may be designed or used to close apertures in arteries or veins (e.g., focal aortic defects, pseudoaneurysms, penetrating ulcers or communicative defects between the true and false lumen in aortic dissections, or arteries or veins themselves). Specifically, the embodiment of FIG. 12 includes a third plate 217, in addition to the first and second plates 214, 216 referenced above. As mentioned above, the first plate 214 is disposed within the first plane 218, and the second plate 216 is disposed in the second plane 220. Also as mentioned above, the first and second planes 218, 220 are parallel to and remote from one another. In addition, in the embodiment of FIG. 12, the third plate 217 is disposed in a third plane 221 that is parallel to and remote from both the first and second planes 218, 220.

Figure 16A:
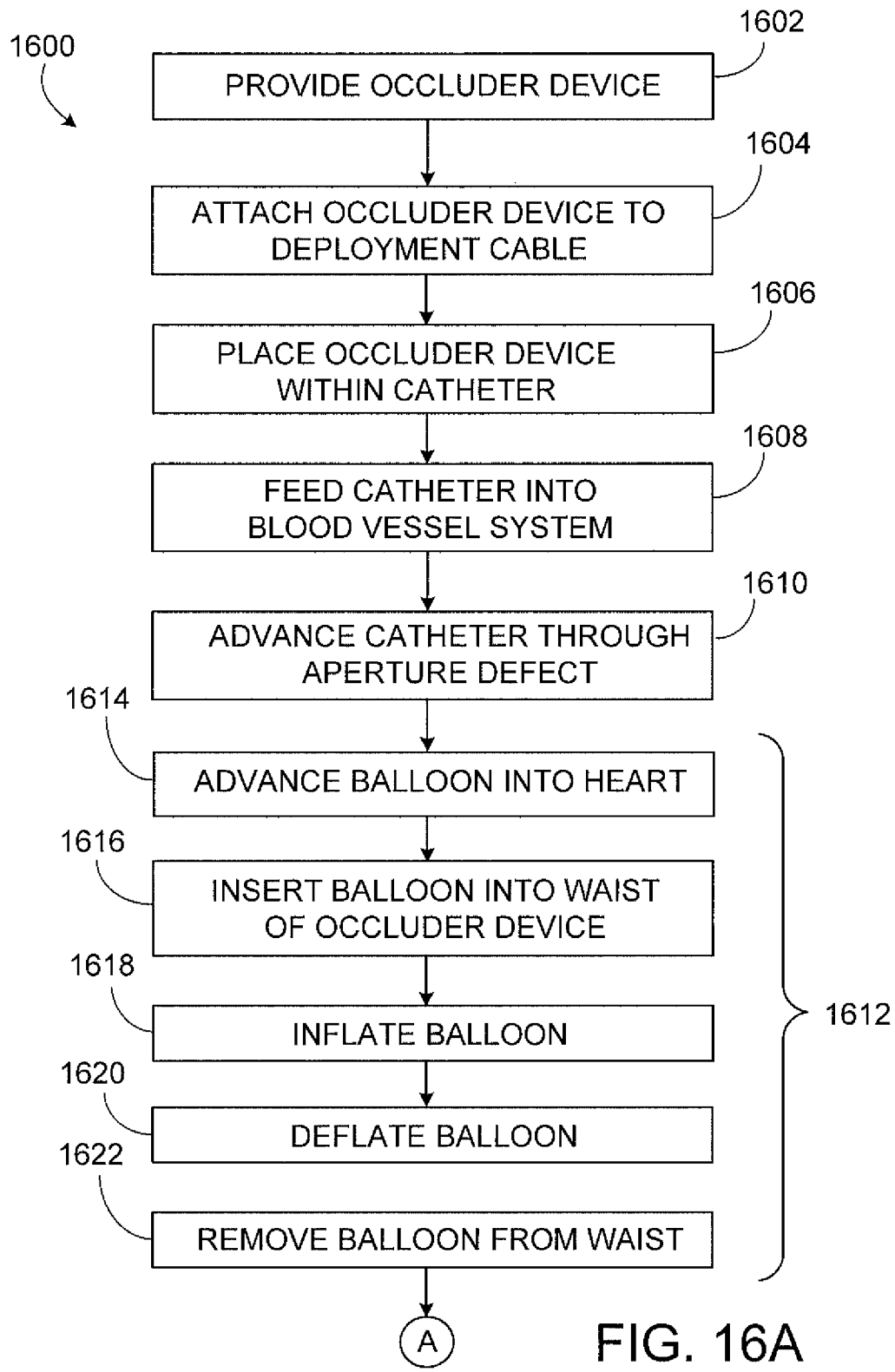
FIG. 16 is a flowchart of an exemplary embodiment of a method for occluding an aperture in tissue or a vessel, and that may be implemented using the occluder devices of FIGS. 2-15.
Figure 16B:
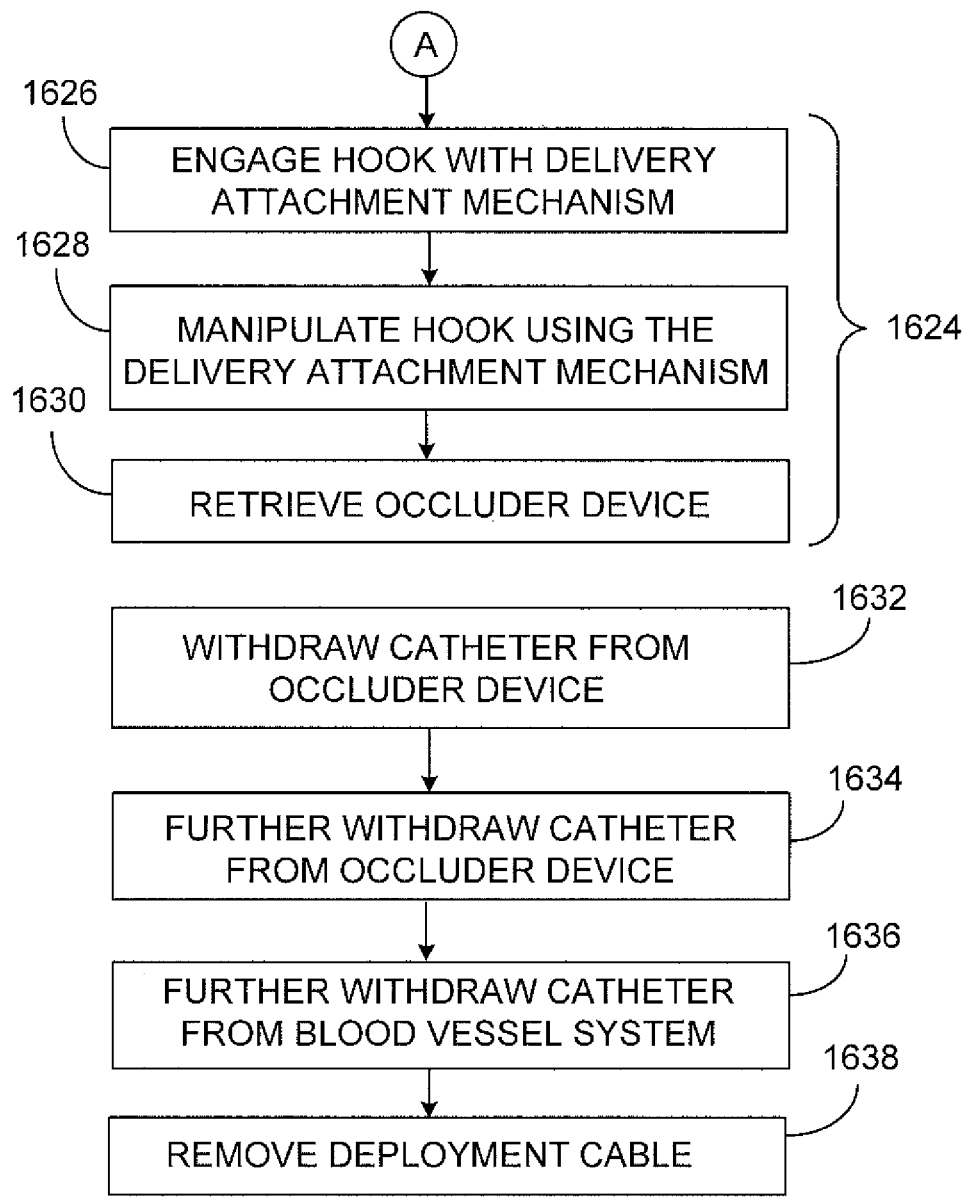

In some embodiments, one or more of the plates may not be parallel to the other of the plates when deployed while in certain embodiments, none of the plates are parallel to the other plates when deployed. In other embodiments and as depicted in FIG. 16, the three (or more) plates may be substantially parallel to each other when deployed.

The embodiment of FIG. 12 also includes a second waist 223, in addition to the first waist 222. As mentioned above, the first waist 222 is formed by first components 224 of the first wire 202 and first components 226 of the second wire 204. In addition, as shown in FIG. 12, the second waist 223 is formed by second, or additional, components 225 of the first wire 202 and second, or additional, components 227 of the second wire 204.

Also in the embodiment of FIG. 12, the first waist 222 is attached between the first and second plates 214, 216, and the second waist 223 is attached between the second and third plates 216, 217. The first, second, and third plates 214, 216, 217 are of unequal sizes, and are arranged in order of increasing size. In some embodiments the third plate 217 is larger than the second plate 216 (for example in terms of diameter and/or surface area), and the second plate 216 is larger than the first plate 214 (for example in terms of diameter and surface area). While the first waist 222 and the second waist 223 may be of approximately equal size as depicted in FIG. 12, in some embodiments the length and/or diameter of the first and second waists may differ. In accord, the number, sizes, and/or shapes of the plates 214, 216, 217 and/or the waists 222, 223 may vary in other embodiments.

In some embodiments, the device includes three or more plates 214, 216, 217, wherein each plate is substantially the same size. In other embodiments, the first and third plates 214 and 217 are of substantially the same size and are larger than the second plate 216. In other embodiments, the first and third plates 214 and 217 are of substantially the same size and are smaller than the second plate 216. In some embodiments, two of the plates are of substantially the same size and are larger than the third plate. In some embodiments, two of the plates are of substantially the same size and are smaller than the third plate.

While in certain embodiments not all of the plates include a covering, in some embodiments, all of the plates include a covering.

In certain embodiments, one or more of the plates 214, 216, 217 of the occluder device 200 of FIG. 12 may be bent and/or inverted. Furthermore, in certain embodiments, a shortest distance between the first and second plates 214, 216 may differ from the shortest distance between the second and third pates 216, 217. In certain embodiments, one or more of the plates 214, 216, 217 may have one or more hook, anchor or barb, or combinations thereof on one or both sides thereof to reduce to eliminate unintentional migration of the device. In some embodiments at least one hook, anchor or barb is affixed to the distal most plate of the device. In some of the embodiments wherein the device has more than two plates, certain embodiments include at least one hook, anchor or barb is affixed to the two distal most plates of the device. The spatial arrangement of hooks, anchors or barbs may be selected according to the location of the aperture to be occluded In some embodiments at least one hook, anchor or barb is affixed to the first and/or second wires. In certain embodiments at least one hook, anchor or barb is positioned on the periphery of the occlusive face. In some embodiments at least one hook, anchor or barb protrudes or projects in a direction from the occlusive face of the device. Some embodiments have at least one hook, anchor or barb protruding or projecting substantially tangent or at an acute angle to the peripheral edge of the occlusive face. Hooks, anchors or barbs can be made of any suitable material. In some embodiments, hooks, anchors or barbs are made of a biocompatible material. In some embodiments hooks, anchors or barbs are constructed of a non-permanent biodegradable or bioabsorbable material. Hooks, anchors and barbs can be attached to the first and/or second wire by any suitable method.

In some vascular implementations, for example, a device may have relatively fewer hooks, anchors or barbs than a device for non-vascular implementation. In some embodiments, the device includes no hooks, anchors or barbs.

Figure 13:
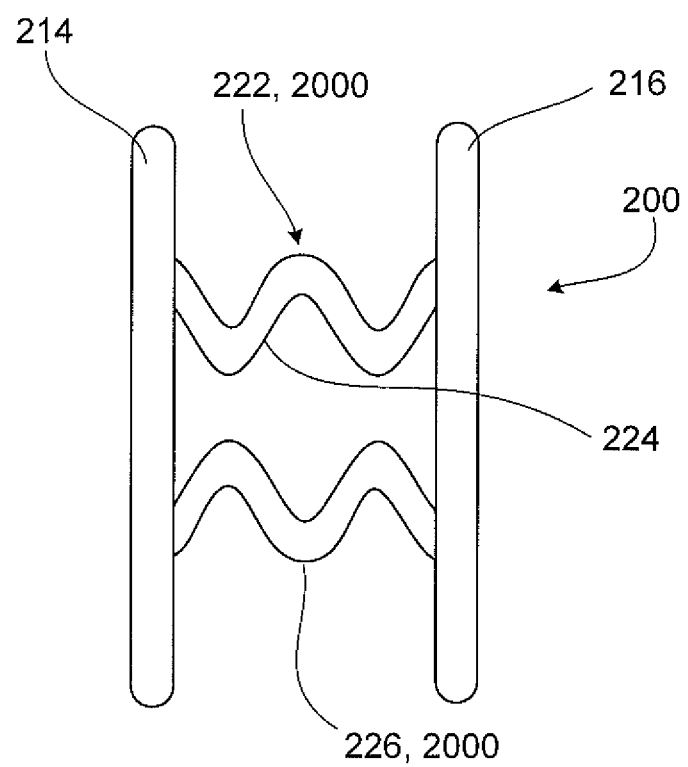
FIG. 13 is a side view of a further exemplary alternative embodiment of an occluder device.
Figure 14:
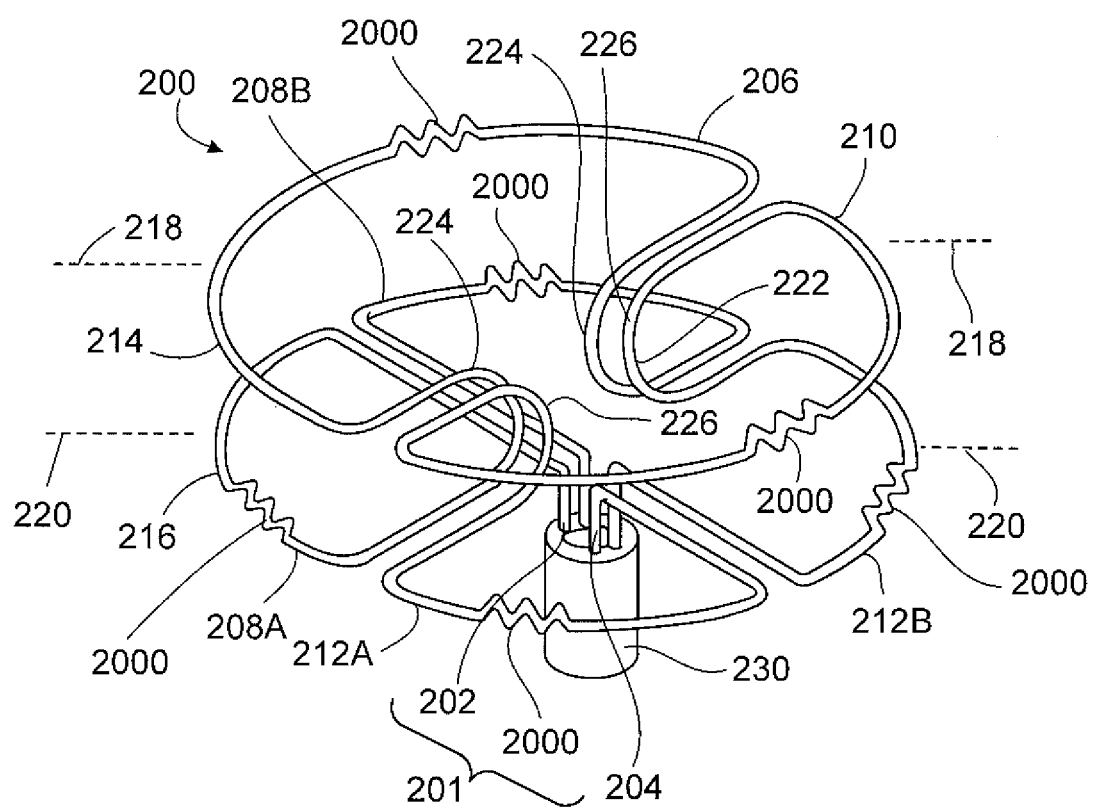
FIG. 14 is a perspective view of another exemplary embodiment of an occluder device.

FIGS. 13 and 14 depict embodiments of an occluder device contemplated herein having a flexible connection. In the embodiment of FIG. 13, the first wire waist components 224 and the second wire waist components 226 are configured such that the waist 222 comprises a flexible connection 2000 between the first and second plates 214, 216. The waist 222 preferably includes a stored length as a result of the flexible connection 2000. As used herein, the term "stored length" means the additional length of the waist 222 to which the waist 222 can be extended from its resting length when the plates 214, 216 are distanced from each other. In certain embodiments, the flexible connection 2000 comprises a spring that is attached between the first and second plates 214, 216. The flexible connection and/or spring may be beneficial, for example, in providing flexibility or greater ability of the occluder device to adjust to apertures of different shapes and sizes With reference to FIG. 14, one or more of the plates of the occluder device may also include one or more strain relief mechanisms, such as springs or flexible connections. As depicted in FIG. 14, both of the plates 214, 216 include flexible connections 2000 similar to those described above in connection with FIG. 13. In certain embodiments, each flexible connection 2000 comprises a spring that is formed within one or more of the geometric forms 206-212. Certain of the plates 214, 216 and/or geometric forms 206-212 may therefore include a stored length similar to that described above in connection with FIG. 13.

While FIG. 14 depicts each of the geometric forms 206-212 as having a flexible connection 2000, in certain embodiments one or more of the geometric forms 206-212 may include a flexible connection while one or more other of the geometric forms 206-212 may not include a flexible connection 2000. Similarly, in certain embodiments, one of the plates 214, 216 may include a flexible connection 2000 while the other of the plates 214, 216 does not. In yet other embodiments, the third plate 217 of FIG. 12 may similarly include a flexible connection 2000, instead of or in addition to one or both of the first and second plates 214, 216.

Figure 15:
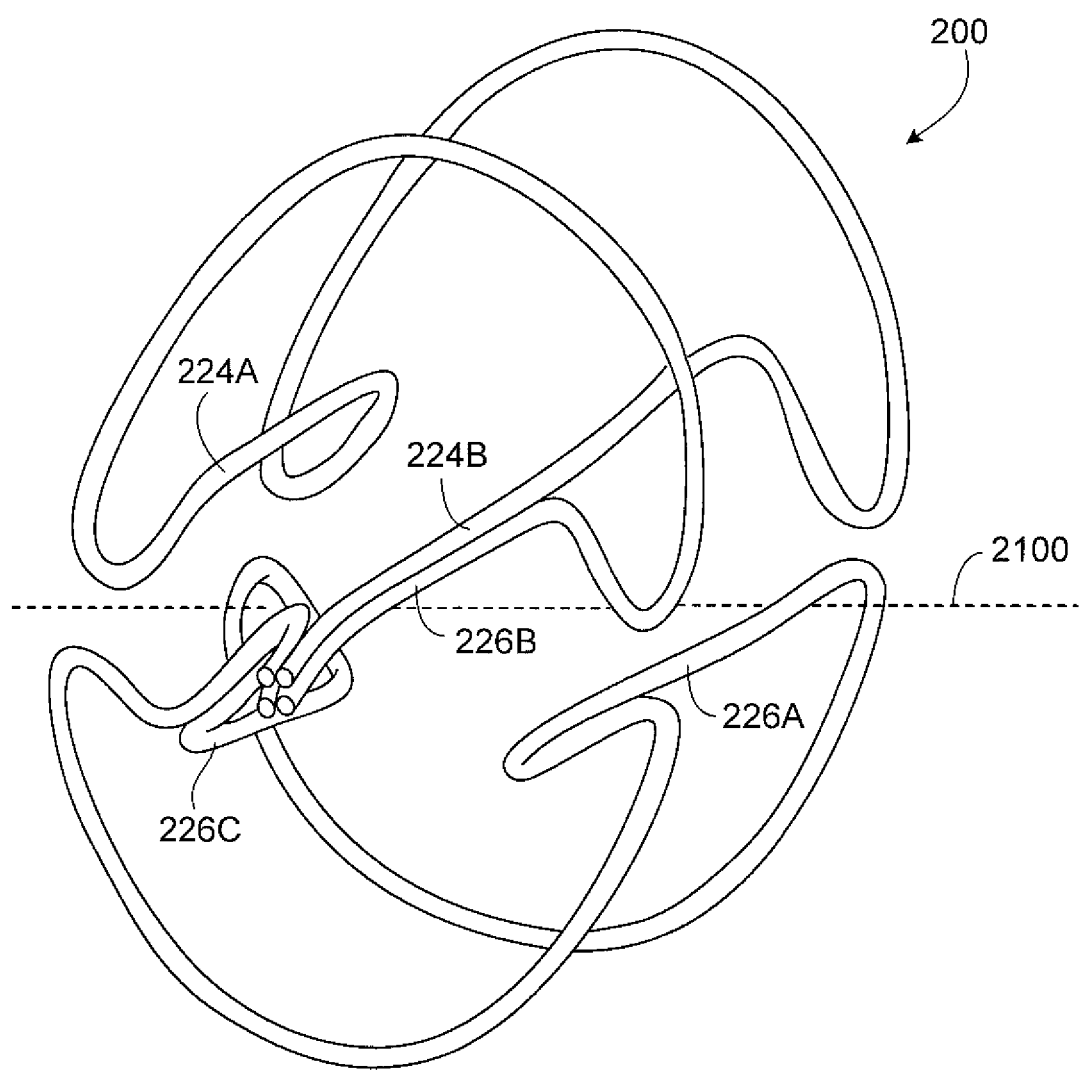
FIG. 15 is a perspective view of yet another exemplary alternative embodiment of an occluder device.

FIG. 15 depicts an embodiment of an occluder device contemplated herein in which the waist is aligned off-center. Specifically, in the embodiment of FIG. 15, the various waist components 224 of the first wire 202 (denoted as 224(A) and 224(B) in FIG. 15) are offset with respect to a center portion or central axis 2100 of the occluder device 200. Similarly, the various waist components 226 of the second wire 204 (denoted as 226(A), 226(B) and 226(C) in FIG. 15) are also offset with respect to the center portion or central axis 2100 of the occluder device 200. In addition, in one version of this embodiment, the first wire 202 crosses a center region of the occluder device 200 at a first point and a second point, and the second wire 204 crosses the center region at a third point and a fourth point.

The embodiment of FIG. 15 provides for increased stability and self-centering of the waist 222. In addition, because of the increased stability and self-centering, in the embodiment of FIG. 15, the plates 214, 216 may be reduced in size as compared with other embodiments. For example, in certain versions of the embodiment of FIG. 2 described earlier, each plate 214, 216 has a surface area that is preferably twice the surface area of the aperture. In contrast, in certain versions of the embodiment of FIG. 15, each plate 214, 216 has a surface area that is only approximately twenty five percent larger than the surface area of the aperture.

FIG. 16 is a flowchart of an exemplary embodiment of a method 1600 for occluding an aperture defect in a heart. The method 1600 can be utilized in connection with the heart 100 of FIG. 1 and the various embodiments of the occluder device 200 of FIGS. 2-15. Specifically, the method 1600 preferably utilizes one or more embodiments of the occluder devices 200 of FIGS. 2-15 to occlude an aperture defect of a heart, such as one or more of the anomalies 110, 112, 114 of the heart 100 depicted in FIG. 1. One skilled in the art would also recognize the method's application for use as a vascular occluder or plug as well as an atrial appendage occluder.

As depicted in FIG. 16, the method 1600 includes the step of providing an occluder device (step 1602). In various embodiments, the occluder device corresponds to the occluder device 200 depicted in any of the embodiments depicted in FIGS. 2-15 and/or described above. The occluder device preferably comprises a first flexible wire (such as wire 202 described above) and a second flexible wire (such as wire 204 described above). Each of the first and second wires is comprised of a shape memory material. Each of the first and second wires is shaped into first and second geometric forms (such as forms 206, 208, 210, and 212 described above) around an inner region such that the first geometric form of the first wire and the first geometric form of the second wire form a first plate (such as pate 214 described above) in a first plane, and the second geometric form 208 of the first wire 202 and the second geometric form 212 of the second wire 204 form a second plate (such as plate 216 described above) in a second plane that is parallel to and remote from the first plane. The first and second plates are separated by a waist (such as waist 222 described above) formed from two portions of the first wire and two portions of the second wire. A sealed covering (such as covering 236 or 238 described above) is preferably disposed over at least one of the first and second plates. The covering provides a seal for the aperture defect (such as one or more of the anomalies 110, 112, 114 of the heart 100 described above). Each of the first and second wires has a first end and a second end. Each of the first and second ends of the first and second wires is connected to a hub (such as hub 230 described above). The hub further comprises a delivery attachment mechanism (for example, that includes or is used in connection with the catheter 242 described above) for attachment to a removable deployment cable (such as deployment cable 240 described above).

The method 1600 also includes the step of attaching the occluder device to the removable deployment cable (step 1604). The occluder device is placed within a flexible delivery catheter (such as the catheter 242 described above) having an open channel (such as the channel 244 described above) (step 1606). The catheter is fed into a blood vessel system (such as a blood vessel system of the heart 100 described above) and advanced via the blood vessel system to the aperture defect in the heart (step 1608). The catheter, with the occluder device disposed within, is similarly advanced through the aperture defect (step 1610).

In some embodiments, a balloon sub-process 1612 is also utilized in occluding the aperture defect in the heart. In some embodiments, depicted in FIG. 16, a balloon is advanced into the heart through the open channel toward the occluder device at the aperture defect (step 1614). The balloon is also inserted into the waist of the occluder device (step 1616). The balloon is then inflated (step 1618), in order to help position the occluder device proximate the heart defect. Once the occluder device is properly positioned, the balloon is deflated (step 1620) and then removed from the waist of the occluder device (step 1622).

In some embodiments, a hook sub-process 1624 may be utilized in occluding the aperture defect in the heart. In some embodiments, as set forth, for example, in FIG. 16, one or more books is engaged with the delivery attachment mechanism (such as the catheter) (step 1626), preferably via a screw system. The hook is manipulated using the delivery attachment mechanism and used to reposition the occluder device (step 1628). In some embodiments, the hook may also be utilized to retrieve the occluder device by exerting force on the delivery attachment mechanism in a direction away from the heart (step 1630).

The catheter next is withdrawn from the occluder device (step 1632). Preferably, the catheter is withdrawn from the occluder device in step 1632 in a manner such that the first plate of the occluder device expands on a first side of the aperture defect. In addition, the catheter is further withdrawn from the occluder device such that the second plate of the occluder device expands on a second side of the aperture defect (step 1634). Preferably, the catheter is withdrawn from the occluder device in step 1634 in a manner, such that the waist of the occluder device expands by memory retention within the aperture defect to self-center the occluder device. The catheter is then withdrawn from the blood vessel system (step 1636), and the deployment cable is removed from the hub of the occluder device (step 1638).

It will be appreciated that certain steps of the method 1600 may vary in certain embodiments. It will also be appreciated that certain steps of the method 1600 may occur in a different order than is depicted in FIG. 16. For example, the optional hook sub-process 1624 may be performed before the optional balloon sub-process 1612. It will similarly be appreciated that certain steps of the method 1600 may occur simultaneously with one another. Additional optional steps may also be performed. For example, in some embodiments the clinician may wish to visualize the location of the device within the aperture. Such visualization may be performed using imaging techniques well known to those of ordinary skill. If the clinician is not satisfied with the positioning of the device based, for example, on visualization of the device, the clinician may choose to remove and/or reposition the device.

Figure 17:
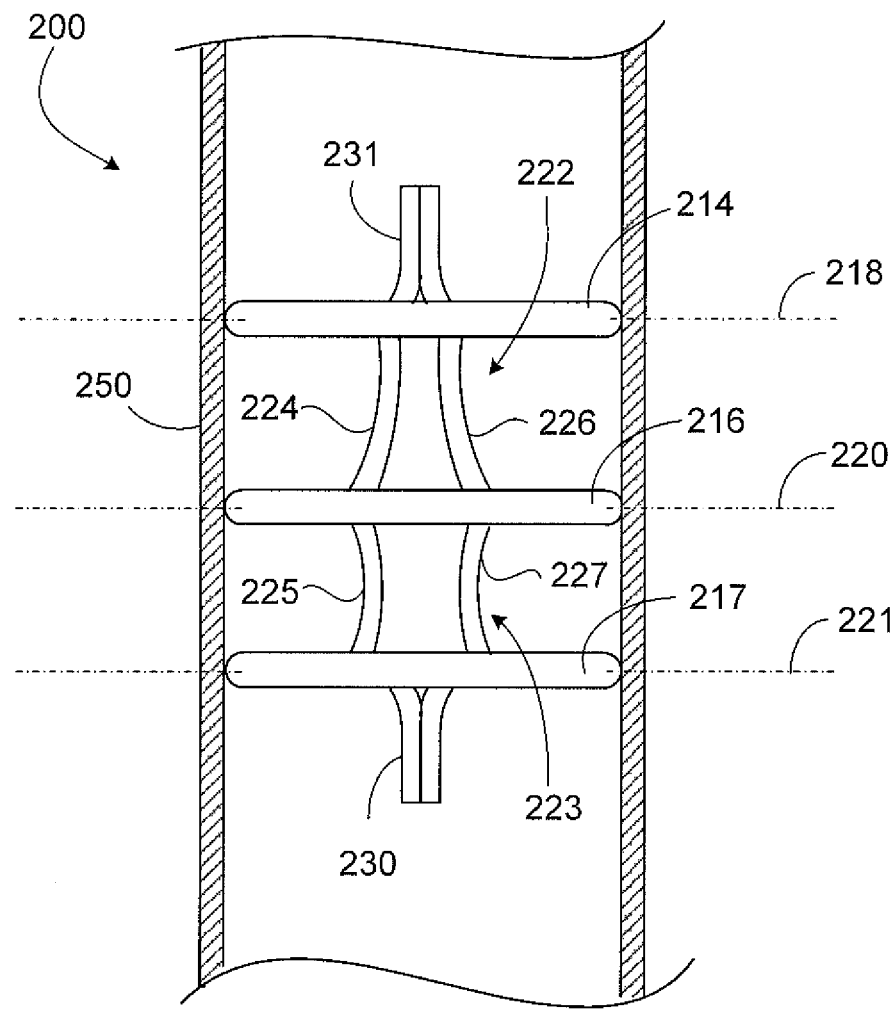
FIG. 17 depicts an exemplary deployment of an occluder device within a vessel.

FIG. 17 depicts an embodiment of an occluder device 200 contemplated herein with three plates 214, 216 and 217 and deployed in a vessel 250. The first waist 222 is formed by first components 224 of the first wire and first components 226 of the second wire. The second waist 223 is formed by second, or additional, components 225 of the first wire and second, or additional, components 227 of the second wire. The first plate 214 is disposed within the first plane 218, and the second plate 216 is disposed in the second plane 220. The first and second planes 218, 220 are parallel to and remote from one another. The third plate 217 is disposed in a third plane 221 that is parallel to and remote from both the first and second planes 218, 220. In the embodiment of FIG. 17 hubs 230, 231 are located at distal and proximal ends of the device.

Other embodiments may comprise any combinations of the embodiments described herein and/or described in the drawings. It is understood that the disclosure is not confined to the particular construction and arrangement of parts herein illustrated and described, but embraces such modified forms thereof as come within the scope of the following claims. Additionally, it will be appreciated that various embodiments may be freely combined together, and/or that various features of different embodiments may be freely combined together.

While several exemplary embodiments have been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A device for occluding an aperture in tissue or a vessel, the device comprising:
    a hub aligned with a central axis of the device and configured to removably attach to a deployment tool for deploying the device at the aperture;
    a first flexible wire attached to the hub and a second flexible wire attached to the hub, wherein each of the first and second wires is comprised of a shape memory material, wherein each of the first and second wires is shaped into a first geometric form, a second geometric form, and a third geometric form, such that, in a deployed configuration, the first geometric form of the first wire and the first geometric form of the second wire form a first plate in a first plane, the second geometric form of the first wire and the second geometric form of the second wire form a second plate in a second plane that is parallel to and remote from the first plane, and the third geometric form of the first wire and the third geometric form of the second wire form a third plate in a third plane that is parallel to and remote from both the first and second planes, and the first and second plates are separated by a first waist formed from two portions of the first wire and two portions of the second wire, and the second and third plates are separated by a second waist formed from an additional two portions of the first wire and an additional two portions of the second wire, and the two portions of the first wire and the two portions of the second wire each include a first curvature and a first length, the additional two portions of the first wire and the additional two portions of the second wire each include a second curvature and a second length, the first length differs from the second length, and the first curvature differs from the second curvature, and
    wherein the additional two portions of the first wire and the additional two portions of the second wire of the first waist and the second waist are substantially centered about a longitudinal axis of the device in the deployed configuration.

2. The device of claim 1, wherein at least two of the first plate, the second plate, and the third plate are of unequal sizes.

3. The device of claim 2, wherein the first plate, the second plate, and the third plate are each of unequal sizes.

4. The device of claim 3, wherein the second plate is larger than the first plate.

5. The device of claim 3, wherein the third plate is larger than the second plate.

6. The device of claim 1, wherein the first plate, the second plate, and the third plate are of equal sizes.

7. The device of claim 1, wherein the first plate has a first surface area; and
    the second plate has a second surface area that is larger than the first surface area.

8. The device of claim 7, wherein the third plate has a third surface area that is larger than the second surface area.

9. The device of claim 1, wherein the first plate has a first diameter; and
    the second plate has a second diameter that is larger than the first diameter.

10. The device of claim 9, wherein the third plate has a third diameter that is larger than the second diameter.

11. The device of claim 1, wherein the first, second, and third and second geometric forms of the first and second wires are generally semi-circular.

12. The device of claim 1, wherein:
    the first plate comprises a first disc;
    the second plate comprises a second disc; and
    the third plate comprises a third disc.

13. The device of claim 1, further comprising:
    a covering arranged on the first plate.

14. The device of claim 1, further comprising: a covering arranged on the second plate.

15. The device of claim 1, further comprising a covering arranged on the first plate and the second plate.

16. The device of claim 15, wherein the covering comprises polytetrafluoroethylene.

17. The device of claim 1, wherein the aperture is a defect selected from the group consisting of a PFO, an ASD, a VSD, and a PDA.

18. The device of claim 1, wherein the aperture is in an artery, vein or atrial appendage.

19. The device of claim 1, further comprising at least one delivery attachment hub, wherein the hub is attached to one or more ends of the first and second wires.

* * * * *